United States Patent
Shen et al.

(10) Patent No.: US 9,187,459 B2
(45) Date of Patent: Nov. 17, 2015

(54) QUINAZOLINE-7-ETHER COMPOUNDS AND METHODS OF USE

(75) Inventors: Wang Shen, San Mateo, CA (US); Wei Xiao, Jiangsu (CN); Jack Maung, Daly City, CA (US); Aimin Zhang, Castro Valley, CA (US); Xiaoling Zheng, Fremont, CA (US); Zhenzhong Wang, Jiangsu (CN); Qingming Guo, Jiangsu (CN); Yingguang Li, Jiangsu (CN)

(73) Assignee: NewGen Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 14/118,200

(22) PCT Filed: May 17, 2012

(86) PCT No.: PCT/US2012/038458
§ 371 (c)(1),
(2), (4) Date: Apr. 3, 2014

(87) PCT Pub. No.: WO2012/158979
PCT Pub. Date: Nov. 22, 2012

(65) Prior Publication Data
US 2014/0221406 A1     Aug. 7, 2014

(30) Foreign Application Priority Data

May 17, 2011   (WO) ................ PCT/CN2011/074165

(51) Int. Cl.
| A01N 43/54 | (2006.01) |
| A61K 31/517 | (2006.01) |
| C07D 401/00 | (2006.01) |
| C07D 239/72 | (2006.01) |
| C07D 405/12 | (2006.01) |
| C07D 493/04 | (2006.01) |

(52) U.S. Cl.
CPC ............ *C07D 405/12* (2013.01); *C07D 493/04* (2013.01)

(58) Field of Classification Search
CPC ..... A01N 43/54; A61K 31/517; C07D 239/72
USPC ................................ 514/266.2; 544/283, 284
See application file for complete search history.

(56) References Cited

U.S. PATENT DOCUMENTS

| 4,062,881 A | 12/1977 | Kugele |
| 5,457,105 A | 10/1995 | Barker |
| 5,521,884 A | 5/1996 | Humphries et al. |
| 5,616,582 A | 4/1997 | Barker |
| 5,747,498 A | 5/1998 | Schnur et al. |
| 5,770,599 A | 6/1998 | Gibson |
| 6,225,318 B1 | 5/2001 | Sobolov-Jaynes et al. |
| 6,391,874 B1 | 5/2002 | Cockerill et al. |
| 6,414,148 B1 | 7/2002 | Thomas et al. |
| 6,627,634 B2 | 9/2003 | Himmelsbach et al. |
| 6,713,485 B2 | 3/2004 | Carter et al. |
| 6,727,256 B1 | 4/2004 | Carter et al. |
| 6,828,320 B2 | 12/2004 | Cockerill et al. |
| 6,894,051 B1 | 5/2005 | Zimmermann et al. |
| 6,900,221 B1 | 5/2005 | Norris et al. |
| 6,958,335 B2 | 10/2005 | Buchdunger et al. |
| 7,157,466 B2 | 1/2007 | McClure et al. |
| 2004/0116422 A1 | 6/2004 | Kitano et al. |
| 2006/0089382 A1 | 4/2006 | Hennequin et al. |
| 2006/0270668 A1 | 11/2006 | Chew et al. |
| 2008/0249087 A1 | 10/2008 | Rotstein et al. |
| 2014/0128417 A1 | 5/2014 | Shen et al. |

FOREIGN PATENT DOCUMENTS

| CN | 1182421 A | 5/1998 |
| CN | 1292788 A | 4/2001 |
| CN | 1310713 A | 8/2001 |
| CN | 1134430 C | 1/2004 |
| CN | 1656081 A | 8/2005 |
| CN | 1812051 A | 8/2006 |
| CN | 1817895 A | 8/2006 |
| CN | 1867564 A | 11/2006 |
| CN | 1305872 C | 3/2007 |
| WO | 96/30347 A1 | 10/1996 |
| WO | 97/38973 A1 | 10/1997 |
| WO | 99/03854 A1 | 1/1999 |
| WO | 99/09016 A1 | 2/1999 |
| WO | 99/35146 A1 | 7/1999 |
| WO | 00/06555 A1 | 2/2000 |
| WO | 02/02552 A1 | 1/2002 |
| WO | WO-02/50043 A1 | 6/2002 |
| WO | 02/066445 A1 | 8/2002 |
| WO | WO-2004/006846 A2 | 1/2004 |
| WO | WO-2005/037824 A2 | 4/2005 |

(Continued)

OTHER PUBLICATIONS

Banker et al (1997).*
Wolff et al (1997).*
Vippagunta (2001).*
International Search Report & Written Opinion received for PCT Patent Application No. PCT/CN2011/074165, mailed on Mar. 8, 2012, 24 pages (12 pages of English Translation and 12 pages of Official Copy).
International Preliminary Report on Patentability received for PCT Patent Application No. PCT/CN2011/074165, mailed on Nov. 28, 2013, 15 pages (7 pages of English Translation and 8 pages of Official Copy).
International Search Report & Written Opinion received for PCT Patent Application No. PCT/US2012/038458, mailed on Jul. 25, 2012, 11 pages.
International Preliminary Report on Patentability received for PCT Patent Application No. PCT/US2012/038458, mailed on Nov. 28, 2013, 9 pages.
International Search Report & Written Opinion received for PCT Patent Application No. PCT/US2012/027614, mailed on Jun. 8, 2012, 8 pages.

(Continued)

*Primary Examiner* — Paul V Ward
(74) *Attorney, Agent, or Firm* — Morrison & Foerster LLP

(57) ABSTRACT

The invention provides quinazoline-7-ether derivatives, particularly 4-anilinyl-6-butenamido-quinazoline-7-ether derivatives that are inhibitors of the receptor protein tyrosine kinases (RTK). The compounds are useful in the treatment of diseases and disorders where RTK activity is implicated such as a hyperproliferative diseases (e.g., cancer). Also provided are methods of preparation of the quinazoline derivatives and methods of use as therapeutic agents alone or in a drug combination.

29 Claims, 4 Drawing Sheets

(56) References Cited

FOREIGN PATENT DOCUMENTS

| WO | 2007054550 A1 | 5/2007 |
| WO | 2007/085638 A1 | 8/2007 |
| WO | WO-2008/033749 A2 | 3/2008 |
| WO | 2009/140863 A1 | 11/2009 |
| WO | 2011/084796 A2 | 7/2011 |
| WO | 2012/021591 A1 | 2/2012 |
| WO | 2012/027960 A1 | 3/2012 |
| WO | 2012/122058 A2 | 9/2012 |

OTHER PUBLICATIONS

International Preliminary Report on Patentability received for PCT Patent Application No. PCT/US2012/027614, mailed on Mar. 20, 2014, 6 pages.

Tsou et al., "Optimization of 6,7-Disubstituted-4-(arylamino)Quinoline-3-Carbonitriles as Orally Active, Irreversible Inhibitors of Human Epidermal Growth Factor Receptor-2 Kinase Activity", Journal of Medicinal Chemistry, vol. 48, No. 4, 2005, pp. 1107-1131.

Baselga et al., "Novel Anticancer Targets: Revisiting ERBB2 and Discovering ERBB3", Nature Reviews Cancer, vol. 9, Jul. 2009, pp. 463-475.

Bendell et al., "Central Nervous System Metastases in Women who Receive Trastuzumab-Based Therapy for Metastatic Breast Carcinoma", Cancer, vol. 97, No. 12, Jun. 15, 2003, pp. 2972-2977.

Bordoni, Rodolfo E., "Afatinib (BIBW-2992): A Novel Dual Egfr/HER2neu Inhibitor with Promising Activity in Non-Small-Cell Lung Cancer", Therapy, vol. 8, No. 1, 2011, pp. 15-22.

Bose et al., "Neratinib: An Oral, Irreversible Dual EGFR/HER2 Inhibitor for Breast and Non-Small Cell Lung Cancer", Expert Opinion on Investigational Drugs, vol. 18, No. 11, 2009, pp. 1735-1751.

Brennan et al., "HER2/Neu: Mechanisms of Dimerization/oligomerization", Oncogene, vol. 19, 2000, pp. 6093-6101.

Broniscer et al., "Plasma and Cerebrospinal Fluid Pharmacokinetics of Erlotinib and Its Active Metabolite OSI-420", Clinical Cancer Research, vol. 13, No. 5, 2007, pp. 1511-1515.

Zhang et al., "ErbB Receptors: from Oncogenes to Targeted Cancer Therapies", The Journal of Clinical Investigation, vol. 117, No. 8, 2007, pp. 2051-2058.

Burgess, Antony W., "EGFR family: Structure Physiology Signalling and Therapeutic Targets", Growth Factors, vol. 26, No. 5, 2008, pp. 263-274.

Cha et al., "Discovery of a Novel Her-1/Her-2 Dual Tyrosine Kinase Inhibitor for the Treatment of Her-1 Selective Inhibitor-Resistant Non-small Cell Lung Cancer", Journal of Medicinal Chemistry, vol. 52, No. 21, 2009, pp. 6880-6888.

Cho, Aesop, "Recent Advances in Oral Prodrug Discovery", Annual Reports in Medicinal Chemistry, vol. 41, 2006, pp. 395-407.

Doebele et al., "New Strategies to Overcome Limitations of Reversible EGFR Tyrosine Kinase Inhibitor Therapy in Non-Small Cell Lung Cancer", Lung Cancer, vol. 69, 2010, pp. 1-12.

Eichler et al., "EGFR Mutation Status and Survival after Diagnosis of Brain Metastasis in Nonsmall Cell Lung Cancer", Neuro-Oncology, vol. 12, No. 11, 2010, pp. 1193-1199.

Heitz et al., "Cerebral Metastases in Metastatic Breast Cancer: Disease-Specific Risk Factors and Survival", Annals of Oncology, vol. 22, 2011, pp. 1571-1581.

Hynes et al., "The Biology of ErbB-2/nue/HER-2 and its Role in Cancer", Biochemical et Biophysical Acta, vol. 1198, 1994, pp. 165-184.

Klapper et al., "Biochemical and Clinical Implications of the ErbB/Her Signaling Network of Growth Factor Receptors", Advanced Cancer Research, vol. 77, 2000, pp. 25-79.

Lassman et al., "Molecular Study of Malignant Gliomas Treated with Epidermal Growth Factor Receptor Inhibitors: Tissue Analysis from North American Brain Tumor Consortium Trials 01-03 and 00-01", Clinical Cancer Research, vol. 11, No. 21, 2005, pp. 7841-7850.

Lemmon, Mark A., "Ligand-Induced ErbB Receptor Dimerization", Experimental Cell Research, vol. 315, No. 4, Feb. 15, 2009, pp. 1-17.

Milanezi et al., "EGFR/HER2 in Breast Cancer: a Biological Approach for Molecular Diagnosis and Therapy", Expert Review of Molecular Diagnostics, vol. 8, No. 4, 2008, pp. 417-434.

Minkovsky et al., "BIBW-2992, a Dual Receptor Tyrosine Kinase Inhibitor for the Treatment of Solid Tumors.", Current Opinion in Investigational Drugs, vol. 9, No. 12, Dec. 2008, pp. 1336-1346.

Moon et al., "Synthesis of Enantiopure Pseudo-l-Vinylcyclopropyl Nucleosides Bearing Quaternary Carbon as Potential Anti-Herpesvirus Agent", Nucleosides, Nucleotides and Nucleic Acids, vol. 26, 2007, pp. 975-978.

Moller et al., "An Improved One-pot Procedure for the Synthesis of Alkynes from Aldehydes", Synlett, Jun. 1996, pp. 521-522.

O'Donovan et al., "EGFR and HER-2 Antagonists in Breast Cancer", Anticancer Research, vol. 27, 2007, pp. 1285-1294.

Ocana et al., "Irreversible Pan-ErbB Tyrosine Kinase Inhibitors and Breast Cancer: Current Status and Future Directions", Cancer Treatment Reviews, vol. 35, 2009, pp. 685-691.

Ohira, Susumu, "Methanolysis of Dimethyl (1-Diazo-2-oxopropyl) Phosphonate: Generation of Dimethyl (Diazomethyl) Phosphonate and Reaction with Carbonyl Compounds", Synthetic Communications, vol. 19, No. 3-4, 1989, pp. 561-564.

Ostrowski et al., "Synthesis and Biological Activity of Tricyclic Analogues of 9-{[cis-1',2'-bis(Hydroxymethyl) Cycloprop-1'-yl]methyl]guanine", Bioorganic & Medicinal Chemistry, vol. 14, 2006, pp. 3535-3542.

Reid et al., "Dual inhibition of ErbB1 (EGFR/HER1) and ErbB2 (HER2/neu)", European Journal of Cancer, vol. 43, 2007, pp. 481-489.

Rewcastle et al., "Tyrosine Kinase Inhibitors. 9. Synthesis and Evaluation of Fused Tricyclic Quinazoline Analogues as Atp Site Inhibitors of the Tyrosine Kinase Activity of the Epidermal Growth Factor Receptor", Journal of Medicinal Chemistry, vol. 39, 1996, pp. pp 918-928.

Sakai et al., "Direct Reduction of Esters to Ethers with an Indium(III) Bromide)Triethylsilane Catalytic System", Synthesis, No. 21, 2008, pp. 3533-3536.

Salomon et al., "Epidermal Growth Factor-Related Peptides and their Receptors in Human Malignancies", Critical Reviews in Oncology/Hematology, vol. 19, 1995, pp. 183-232.

Smaill et al., "Tyrosine Kinase Inhibitors. 17. Irreversible Inhibitors of the Epidermal Growth Factor Receptor: 4(Phenylamino)quinazoline- and 4-(Phenylamino)pyrido[3,2-d]pyrimidine-6-acrylamides Bearing Additional Solubilizing Functions", Journal of Medicinal Chemistry, vol. 43, 2000, pp. 1380-1397.

Smith et al., "Chapter 4 of Mar.'s Advanced Organic Chemistry: Reactions, Mechanisms and Structure", John Wiley & Sons, 6th edition, 2007, 118 pages.

Stella et al., "Prodrugs: Challenges and Rewards, Part 1", American Association of Pharmaceutical Scientists, 2007, 10 pages.

Steeg et al., "Brain Metastases as Preventive and Therapeutic Targets", Nature Reviews Cancer, vol. 11, May 2011, pp. 352-363.

Extended European Search Report (includes Supplementary European Search Report and Search Opinion) received for European Patent Application No. 12786332.2, mailed on Oct. 21, 2014, 6 pages.

Extended European Search Report (includes Supplementary European Search Report and Search Opinion) received for European Patent Application No. 12754325.4, mailed on Jan. 09, 2015, 8 pages.

Blackhall et al., "Erlotinib in Non-small Cell Lung Cancer: A Review", Expert Opinion on Pharmacotherapy, vol. 6, No. 6, 2005, pp. 995-1002.

Li et al., "BIBW2992, An Irreversible EGFR/HER2 Inhibitor Highly Effective in Preclinical Lung Cancer Models", Oncogene, vol. 27, No. 34, 2008, pp. 4702-4711.

* cited by examiner

QUINAZOLINE-7-ETHER COMPOUNDS AND METHODS OF USE

CROSS-REFERENCE TO RELATED APPLICATIONS

This application is a national phase application under 35 U.S.C. §371 of International Application No. PCT/US2012/038458 filed May 17, 2012, which claims priority to International Patent Application No. PCT/CN2011/074165 filed May 17, 2011, the disclosure of each of which is incorporated herein by reference in its entirety.

FIELD OF THE INVENTION

The invention relates to the pharmaceutical field, in particular relates to the preparation of 4-anilinyl-6-butenamidoyl-7-alkoxy-quinazolin derivatives and the pharmaceutical composition containing these derivatives and their use as therapeutic agents particularly as inhibitors of pan-ErbB family kinases.

BACKGROUND OF THE INVENTION

Cellular signal transduction is a fundamental mechanism. During the signal transduction, the extracellular stimulation is transmitted intracellularly, to modulate various cellular processes including cell proliferation, differentiation, apoptosis and cell migration. A lot of signal transductions are mediated by growth factors binding to protein tyrosine kinase (PTK) trans-membrane receptor protein tyrosine kinases (RTK).

When RTK is inappropriately or constitutively activated, abnormal RTK activity such as that caused by overexpression or mutations results in uncontrolled cell proliferation or differentiation, and leads to diseases. Known diseases caused by abnormal activity of RTKs include psoriasis, rheumatoid arthritis, many types of cancer, angiogenesis, atherosclerosis and so on. RTK is comprised of many families, and one of them is ErbB family which is comprised of EGFr (also named ErbB1), HER2 (ErbB2), HER3 (ErbB3) and HER4 (ErbB4). These RTKs contain an extracellular glycoxylated domain for ligand binding, a transmembrane domain, and an intracellular cytoplasma catalyticaldomain capable of phosphorylating tyrosines of proteins. HER3 does not have an intracellular cytoplasma catalyticaldomain capable of phosphorylating tyrosines of protein. The RTK catalytic activity can be activated either by receptor overexpression or by ligand mediated dimerization. The ErB family RTKs can form homodimers or heterodimers. An example of homodimerization comes from EGFr binding with EGF family ligand (including EGF, transforming growth factor, becellulin epiregulin, etc). The heterodimerization between EGFr family RTKs can be accelerated by heregulin (also named nerregulin) binding. Even though HER3 does not have receptor kinase activity, its heterodimerization with HER2 or HER4 can greatly enhance the receptor kinase dimerization and the tyrosine phosphoryzation catalytic activity. Overactivation of EGFr has been associated with proliferation diseases such as NSCLC, bladder cancer, head and neck cancer, brain cancer and other cancers, while HER2 hyperactivity has been associated with breast cancer, ovarian cancer, uterine cancer, gastric cancer, and pancreatic cancer, etc. Therefore, inhibition of ErbB family RTKs may provide a treatment of the diseases associated with characteristic abnormal erbB family RTK activities. Many publications have discussed the biological activities of erB family RTKs, and their relationship with different diseases, such as the following papers and patents: Reid, A., et al. *Eur. J. Cancer,* 2007, 43, 481; Doebele, R. C., et al. *Lung Cancer,* 2010, 69, 1-12; Ocana, A.; Amir, E. *Cancer Treat. Rev.* 2009, 35, 685-91; Minkovsky, N., et al. *Current Opinion in Investigational Drugs* 2008, 9, 1336-1346; WO2002/66445, WO1999/09016, U.S. Pat. No. 6,627,634, etc.

Many patents have revealed RTK inhibitors or quinazoline derivatives related technology, for examples: WO9630347 (Chinese patent application CN96102992.7) revealed some 4-anilinylquinazoline derivatives for the treatment of excessive proliferative diseases. WO9738973 (Chinese application CN97194458) and WO2009/140863 (Chinese application CN2009000557) disclosed the preparation and pharmaceutical application of irreversible tyrosine kinase inhibitors. WO0006555 (Chinese application CN99808949) disclosed that certain quinazoline derivatives inhibited RTK activities. WO9935146 (Chinese application CN99803887) disclosed a series of fused heteryl aromatic compounds including quinazolines as active as RTK kinase inhibitors. In addition, Chinese patent applications such as CN01817895, CN93103556, CN98807303, CN96193526, CN01812051, CN99803887, CN0410089867, CN03811739; U.S. Pat. No. 5,521,884, U.S. Pat. No. 6,894,051, U.S. Pat. No. 6,958,335, U.S. Pat. No. 5,457,105, U.S. Pat. No. 5,616,582, U.S. Pat. No. 5,770,599, U.S. Pat. No. 5,747,498, U.S. Pat. No. 6,900,221, U.S. Pat. No. 6,391,874, U.S. Pat. No. 6,713,485, U.S. Pat. No. 6,727,256, U.S. Pat. No. 6,828,320, U.S. Pat. No. 7,157,466 all disclosed that various types of quinazoline derivatives could inhibit the activities of many types of RTKs. Several quinazoline based kinase inhibitors have been approved in US, Europe and many other countries for the treatment of cancer, for example, gefitinib (trade name Irresa), erlotinib (trade name Tarceva), lapatinib (trade name Tykerb), etc. With continued improvement in research of biological mechanism, diagnosis and treatment of cancer treatment of proliferative diseases, especially cancer, is becoming more precise, targeted and personalized. Therefore, there is still an urgent need for clinical applications to develop highly efficacious and highly targeted drugs against proliferative diseases and cancer.

BRIEF SUMMARY OF THE INVENTION

This invention provides for quinazoline-7-ether derivatives of the formula (I) or any variations detailed herein, and pharmaceutically acceptable salts and prodrugs thereof, that are useful in the treatment of cancers where RTK is implicated. Specifically, the present invention relates to compounds of the formula (I), or any variations detailed herein, that act as EGFR and ErbB2 inhibitors. Also provided are formulations containing compounds of the formula (I) and methods of using the compounds in treating an individual in need thereof. In addition, described are processes for preparing the inhibitory compounds of the formula (I).

In one aspect, provided is a compound of the formula (I):

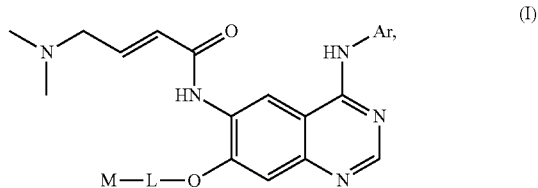

or a salt, solvate, polymorph, metabolite or prodrug thereof, wherein:

Ar is a monocyclic aryl or monocyclic heteroaryl, optionally substituted with 0 to 4 substituents independently selected from the group consisting of halogen, trifluoromethyl, trifluoromethoxy, $C_1$-$C_3$ alkyl, ethynyl, ethenyl, $C_1$-$C_3$ alkoxy, —O(CH$_2$)$_n$Ar$^1$; —(CH$_2$)$_m$Ar$^2$ and —S(O)$_2$Ar$^3$;

m and n are independently 0 or 1;

each Ar$^1$, Ar$^2$ and Ar$^3$ is independently a monocyclic aryl or 5 or 6 membered heteroaryl, where each aryl or heteroaryl is optionally substituted with 0 to 3 substituents independently selected from the group consisting of halogen, trifluoromethyl, trifluoromethoxy, $C_1$-$C_3$ alkyl, $C_2$-$C_3$ alkynyl, $C_2$-$C_3$ alkenyl and $C_1$-$C_3$ alkoxy;

L is a bond or CH$_2$; and

M is a 6-10 membered bicyclic heterocycle containing one or more annular heteroatoms independently selected from O, N and S, optionally substituted with one or more substituents independently selected from the group consisting of halogen, $C_1$-$C_3$ alkyl, hydroxyl and $C_1$-$C_3$ alkoxy.

In some embodiments, the compound is of the formula (I), or salt, solvate, polymorph, metabolite or prodrug thereof, wherein Ar is 3-chloro-4-fluorophenyl, L is a bond or CH$_2$, and M is hexahydro-3-methoxyfuro[3,2-b]furan-6-yl, 3-oxabicyclo[3.1.0]hexan-6-yl or 3-oxabicyclo[3.1.0]hexan-1-yl. In a particular variation, L is CH$_2$ and M is 3-oxabicyclo[3.1.0]hexan-6-yl.

In another aspect, provided are methods for treating receptor protein tyrosine kinase-related disease in an individual in need thereof comprising administering to the individual an effective amount of a compound of the formula (I), or salt, solvate, polymorph, metabolite or prodrug thereof. In some embodiments, the receptor protein tyrosine kinase-related disease is a cancer (e.g., breast cancer, colorectal cancer, lung cancer, papillary carcinoma, prostate cancer, lymphoma, pancreatic cancer, ovarian cancer, cervical cancer, central nervous system cancer, osteogenic sarcoma, kidney cancer, liver cancer, bladder cancer, gastric cancer, head and neck squamous cell carcinoma, melanoma, or leukemia).

The invention also provides pharmaceutically acceptable salts, pharmaceutically acceptable prodrugs, and pharmaceutically active metabolites of the compound of the formula (I) or any variations described herein. Methods of making the compounds of the formula (I) are also described.

Also provided are pharmaceutical compositions comprising a compound detailed herein such as a compound of the formula (I), or a pharmaceutically acceptable prodrug, pharmaceutically active metabolite, or pharmaceutically acceptable salt thereof, and a pharmaceutically acceptable carrier or excipient. Compounds as detailed herein or a pharmaceutically acceptable salt thereof are also provided for the manufacture of a medicament for the treatment of cancer. Kits comprising a compound detailed herein are provided, which optionally includes instructions for use in the methods detailed herein (e.g., in treating a receptor protein tyrosine kinase-related disease such as cancer).

It is to be understood that one, some, or all of the features of the various embodiments described herein may be combined to form other embodiments of the present invention. These and other aspects of the invention will become apparent to one of skill in the art.

DETAILED DESCRIPTION OF THE INVENTION

Figure 1:
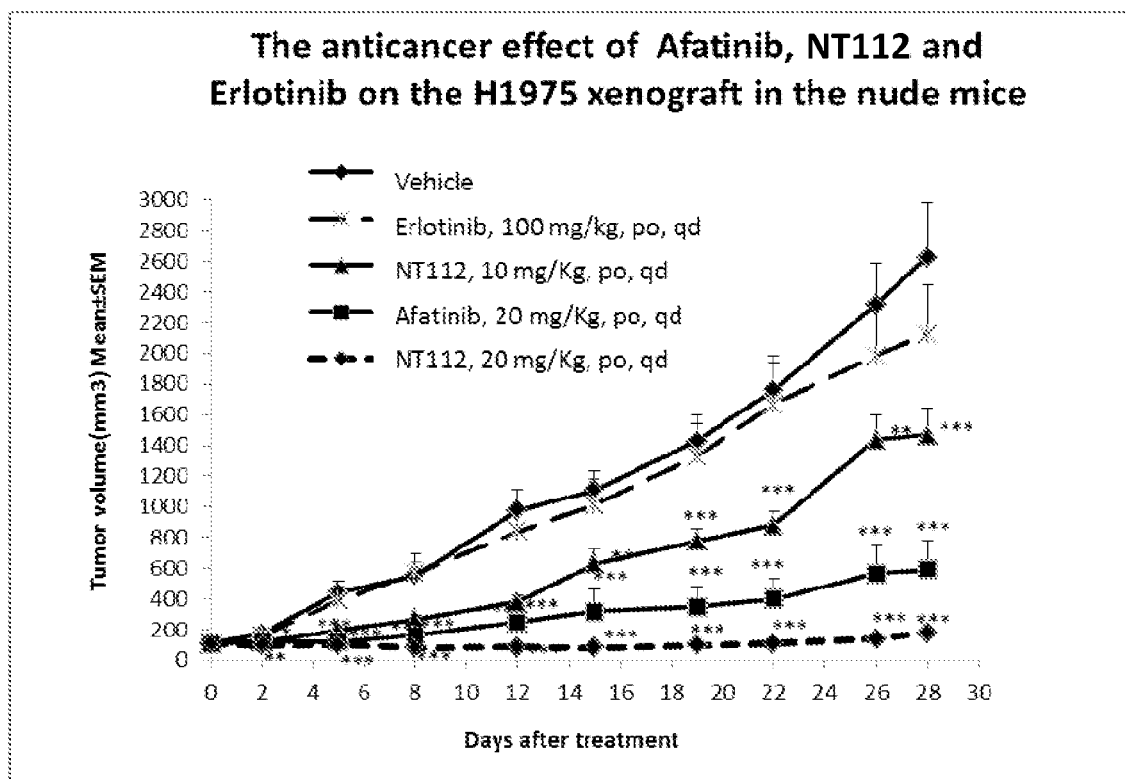
FIG. 1 shows the anticancer effect of Compound NT112 on the H1975 xenograft in the nude mice in comparison with erlotinib and afatinib.

This invention provides compounds that are inhibitors of receptor tyrosine kinases, and have advantageous pharmacokinetic properties. Compounds and compositions provided herein have superior pharmacokinetic properties to those of the standard therapies (e.g., afatinib) and better bioavailability, thus may have better efficacy and/or require lower doses to achieve the same therapeutic effect.

DEFINITIONS

Except as expressly defined otherwise, the following definition of terms is employed throughout this specification.

The term "alkyl" as used herein refers to a saturated linear or branched-chain hydrocarbon of 1 to 20 carbon atoms. Preferred are alkyl radicals of 1 to 6 carbon atoms ("$C_1$-$C_6$ alkyl"), such as methyl, ethyl, propyl, isopropyl, butyl, isobutyl, tert-butyl, pentyl, and the like. More preferred are lower alkyl radicals of 1 to 3 carbon atoms ("$C_1$-$C_3$ alkyl"), such as methyl, ethyl, propyl, isopropyl. An alkyl radical may be unsubstituted or substituted with one or more substituents described herein, such as hydroxyl, halogen and the like.

"Aryl" refers to an aromatic carbocyclic group having at least a one aromatic ring, and an aromatic ring system is a conjugated π electron system.

"Heteroaryl" as used herein refers to an aromatic radical containing 1-4 ring heteroatoms, the remaining ring atoms being carbon.

"Bicyclic heterocycle" as used herein refers to a fused or spiro bicyclic group, containing at least 6-10 ring atoms, with 1-3 ring heteroatoms selected from N, O or S(O)$_n$ (where n is 0, 1 or 2), the remaining ring atoms being carbon. The bicyclic heterocycle group may contain one or more double bonds. The bicyclic heterocycle group may be substituted or unsubstituted, or optionally substituted with one or more substituents, preferably with one, two or three, and even more preferably with one or two substituents independently selected from lower alkyl, trifluoromethyl, halogen, lower alkoxy, cyano, and the like.

"Halogen" refers to fluorine, chlorine, bromine, or iodine. Likewise, the term "halo" represents fluoro, chloro, bromo or iodo. Preferred "halogens" are fluorine and chlorine.

"Hydroxyl" refers to the "—OH" group.

"Alkoxy" refers to "—O-alkyl", including but not limited to methoxy, ethoxy, propyloxy, cyclopropyloxy, butoxy, cyclobutyloxy, and the like.

"Optional" means that the event or situation described thereafter may occur but may not necessarily occur. The terms "optionally substituted" and "substituted or unsubstituted" used herein are exchangeable. The term "substituted" in general means that one or more hydrogen atoms of the described structure are replaced by specific substituents. Except as expressly defined otherwise, an optionally substituted group may have one substituent substituted at each substitutable position. When a given structure has more than one position substitutable with one or more substituting groups, the substituents can be the same or different at each position. The substituents include, but are not limited to, hydroxyl, amino, halogen, cyano, aryl, heteroaryl, alkoxy, alkyl, alkenyl, alkynyl, heterocyclyl, thiol, nitro, aryloxyl, and the like.

Compounds

In one aspect, provided is a compound of the formula (I):

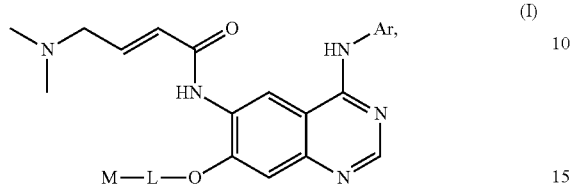

or a salt, solvate, polymorph, metabolite or prodrug thereof, wherein:

Ar is a monocyclic aryl or monocyclic heteroaryl, optionally substituted with 0 to 4 substituents independently selected from the group consisting of halogen, trifluoromethyl, trifluoromethoxy, $C_1$-$C_3$ alkyl, ethynyl, ethenyl, $C_1$-$C_3$ alkoxy, —O(CH$_2$)$_n$Ar$^1$; —(CH$_2$)$_m$Ar$^2$ and —S(O)$_2$Ar$^3$;

m and n are independently 0 or 1;

each Ar$^1$, Ar$^2$ and Ar$^3$ is independently a monocyclic aryl or 5 or 6 membered heteroaryl, where each aryl or heteroaryl is optionally substituted with 0 to 3 substituents independently selected from the group consisting of halogen, trifluoromethyl, trifluoromethoxy, $C_1$-$C_3$ alkyl, $C_2$-$C_3$ alkynyl, $C_2$-$C_3$ alkenyl and $C_1$-$C_3$ alkoxy;

L is a bond or CH$_2$; and

M is a 6-10 membered bicyclic heterocycle containing one or more annular heteroatoms independently selected from O, N and S, optionally substituted with one or more substituents independently selected from the group consisting of halogen, $C_1$-$C_3$ alkyl, hydroxyl and $C_1$-$C_3$ alkoxy.

In some embodiments, the compound is of the formula (I), or salt, solvate, polymorph, metabolite or prodrug thereof, wherein Ar is a phenyl optionally substituted with 0 to 4 substituents independently selected from the group consisting of halogen, trifluoromethyl, trifluoromethoxy, $C_1$-$C_3$ alkyl, ethynyl, ethenyl, $C_1$-$C_3$ alkoxy, —O(CH$_2$)$_n$Ar$^1$; —(CH$_2$)$_m$Ar$^2$ and —S(O)$_2$Ar$^3$. In some embodiments, Ar is a phenyl substituted with 1 to 3 substituents independently selected from the group consisting of halogen, trifluoromethyl, trifluoromethoxy, $C_1$-$C_3$ alkyl, ethynyl, ethenyl, $C_1$-$C_3$ alkoxy, —O(CH$_2$)$_n$Ar$^1$; —(CH$_2$)$_m$Ar$^2$ and —S(O)$_2$Ar$^3$, where Ar$^1$, Ar$^2$, Ar$^3$, m and n are as defined for formula (I).

In some embodiments, Ar is a substituted phenyl selected from the group consisting of:

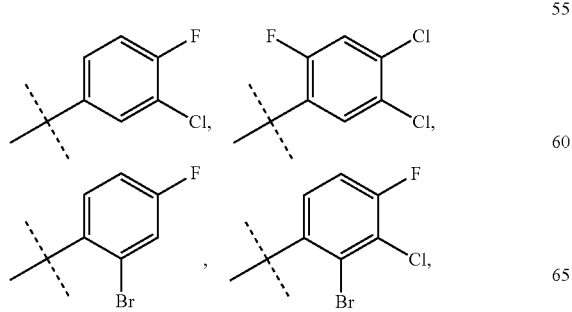

-continued

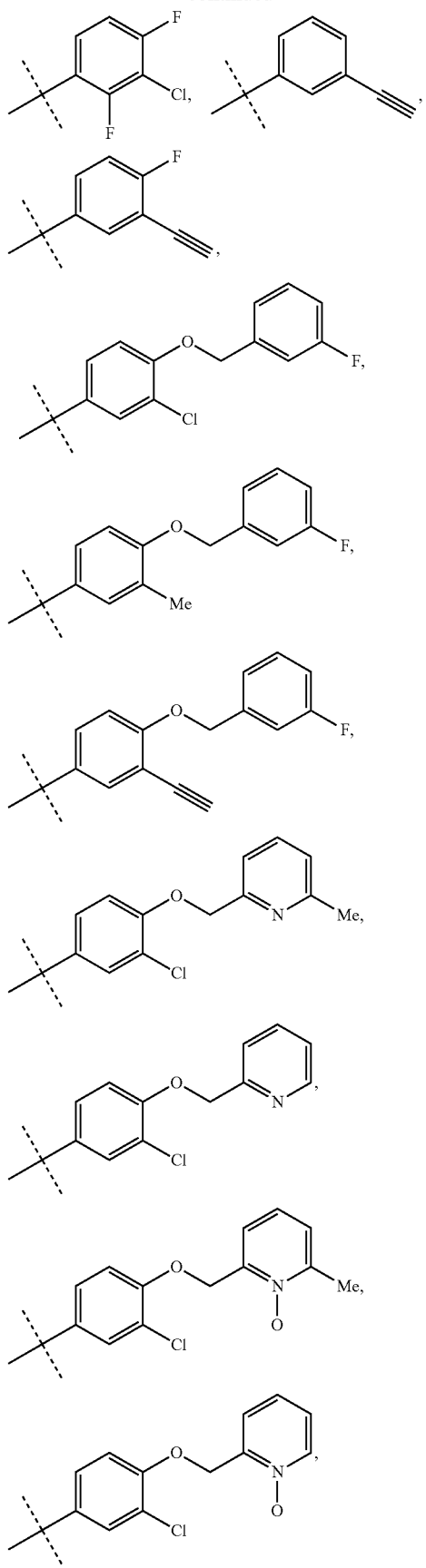

-continued
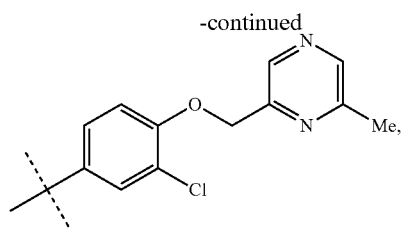
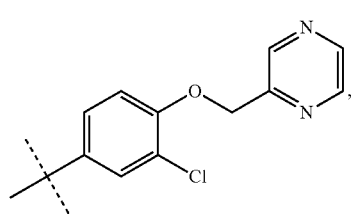
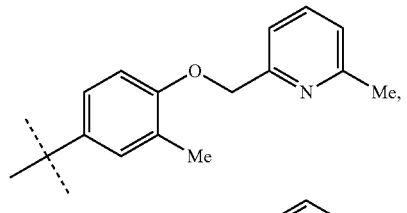
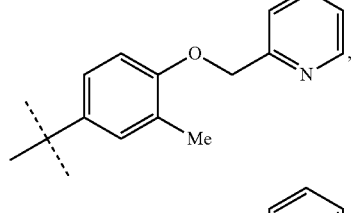
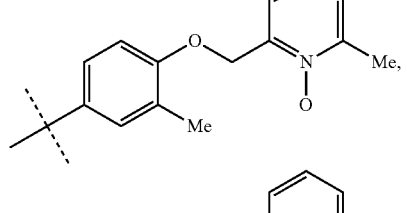
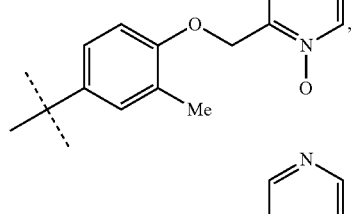
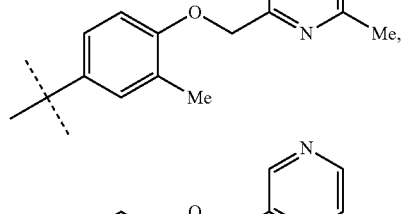
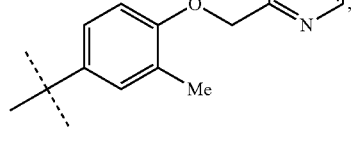
-continued
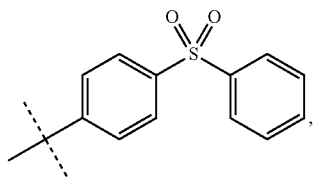
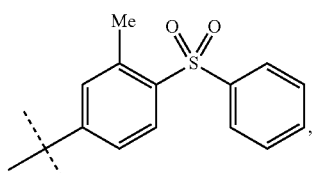
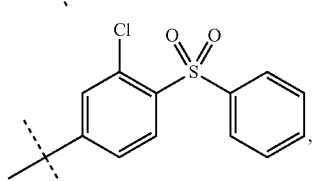
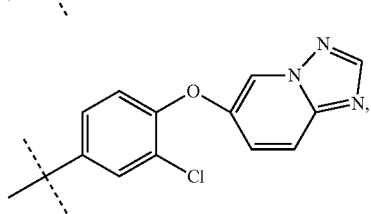
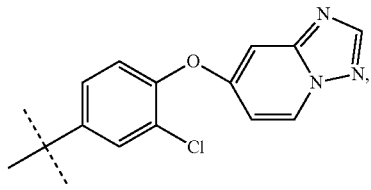
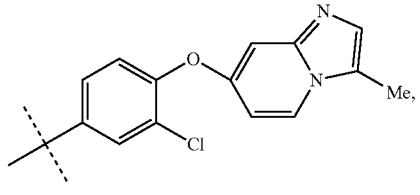
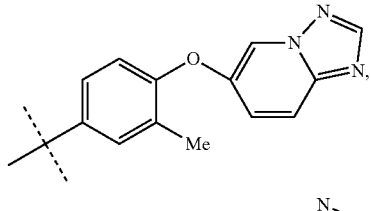
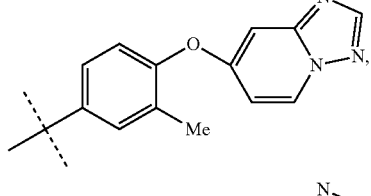
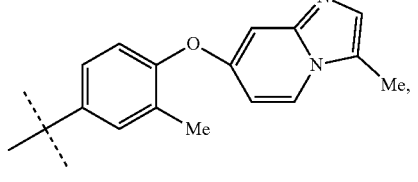

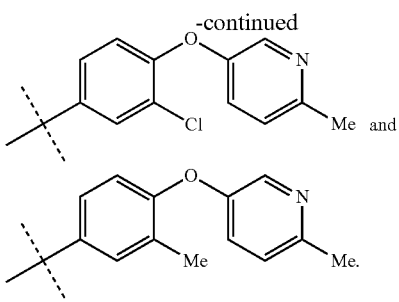

In some preferred embodiments, Ar is 3-chloro-4-fluorophenyl.

In some embodiments, Ar is a monocyclic heteroaryl optionally substituted with 0 to 4 substituents independently selected from the group consisting of halogen, trifluoromethyl, trifluoromethoxy, $C_1$-$C_3$ alkyl, ethynyl, ethenyl, $C_1$-$C_3$ alkoxy, —O($CH_2$)$_n$$Ar^1$; —($CH_2$)$_m$$Ar^2$ and —S(O)$_2$$Ar^3$, where $Ar^1$, $Ar^2$, $Ar^3$, m and n are as defined for formula (I).

In some embodiments, Ar is a substituted heteroaryl selected from the group consisting of:

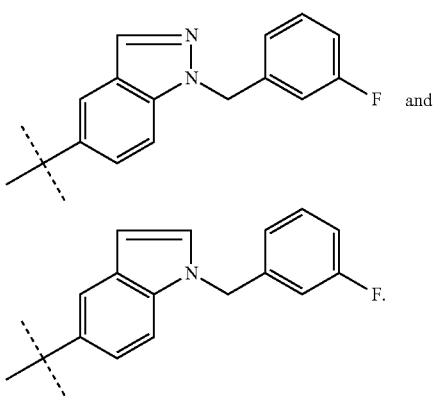

In some embodiments, the compound is of the formula (I), or salt, solvate, polymorph, metabolite or prodrug thereof, wherein L is a bond or $CH_2$. In some embodiments, L is a bond. In some embodiments, L is $CH_2$.

In some embodiments, the compound is of the formula (I), or salt, solvate, polymorph, metabolite or prodrug thereof, wherein M is a 6-10 membered bicyclic heterocycle containing one or more annular heteroatoms independently selected from O, N and S, substituted with one or more substituents selected from the group consisting of halogen, $C_1$-$C_3$ alkyl, hydroxyl and $C_1$-$C_3$ alkoxy. In some of these embodiments, M is

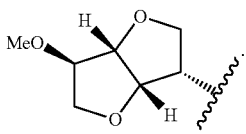

In some embodiments, M is an unsubstituted 6-10 membered bicyclic heterocycle containing one or more annular heteroatoms independently selected from O, N and S. In some of these embodiments, M is a 6-10 membered bicyclic heterocycle containing one annular heteroatom selected from O, N and S. In some of these embodiments, M is a 6-10 membered bicyclic heterocycle containing one annular heteroatom which is oxygen, e.g., 3-oxabicyclo[3.1.0]hexan-6-yl and 3-oxabicyclo[3.1.0]hexan-1-yl.

It is understood and clearly conveyed herein that each and every variation of Ar, L or M described herein may be combined with each and every variation of other variables described herein, where applicable, as if each and every combination were listed separately. For example, in one variation, provided is a compound of the formula (I), or salt, solvate, polymorph, metabolite or prodrug thereof, wherein Ar is 3-chloro-4-fluorophenyl, L is a bond or $CH_2$, and M is hexahydro-3-methoxyfuro[3,2-b]furan-6-yl, 3-oxabicyclo[3.1.0]hexan-6-yl or 3-oxabicyclo[3.1.0]hexan-1-yl. In a particular variation, L is $CH_2$ and M is 3-oxabicyclo[3.1.0]hexan-6-yl.

In some embodiments, the compound is of formula (I), or salt, solvate, polymorph, metabolite or prodrug thereof, wherein the compound is selected from the group consisting of:

(E)-N-(7-((3R,3aS,6S,6aS)-hexahydro-3-methoxyfuro[3,2-b]furan-6-yloxy)-4-(3-chloro-4-fluorophenylamino)quinazolin-6-yl)-4-(dimethylamino)but-2-enamide, (Compound 1);

(E)-N-(7-((3-oxa-bicyclo[3.1.0]hexan-6-yl)methoxy)-4-(3-chloro-4-fluorophenylamino)quinazolin-6-yl)-4-(dimethylamino)but-2-enamide, (Compound 2);

(E)-N-(7-(((1R,5S,6σ-3-oxa-bicyclo[3.1.0]hexan-6-yl)methoxy)-4-(3-chloro-4-fluorophenylamino)quinazolin-6-yl)-4-(dimethylamino)but-2-enamide, (Compound 2-A);

(E)-N-(7-(((1R,5S,6s)-3-oxa-bicyclo[3.1.0]hexan-6-yl)methoxy)-4-(3-chloro-4-fluorophenylamino)quinazolin-6-yl)-4-(dimethylamino)but-2-enamide, (Compound 2-B);

(E)-N-(7-(((1S,5S)-3-oxa-bicyclo[3.1.0]hexan-1-yl)methoxy)-4-(3-chloro-4-fluorophenylamino)quinazolin-6-yl)-4-(dimethylamino)but-2-enamide, (Compound 3);

(E)-N-(7-(((1R,5R)-3-oxa-bicyclo[3.1.0]hexan-1-yl)methoxy)-4-(3-chloro-4-fluorophenylamino)quinazolin-6-yl)-4-(dimethylamino)but-2-enamide, (Compound 4); and (E)-N-(7-((3-oxa-bicyclo[3.1.0]hexan-1-yl)methoxy)-4-(3-chloro-4-fluorophenylamino)quinazolin-6-yl)-4-(dimethylamino)but-2-enamide, (Compound 5).

In some embodiments, the compound is of formula:

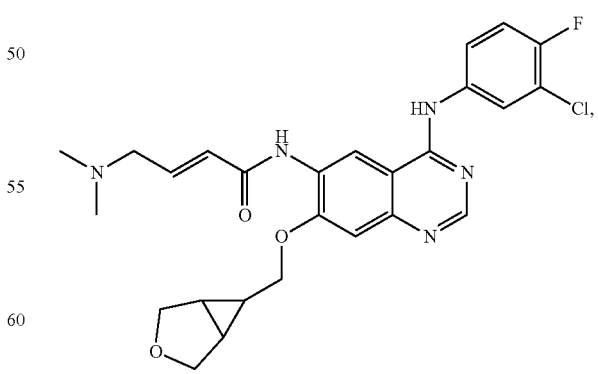

or a salt, solvate, polymorph, metabolite or prodrug thereof. The invention embraces all stereoisomers, or mixtures thereof, such as a compound of the formula (2-A) or (2-B), or a mixture thereof:

(2-A)

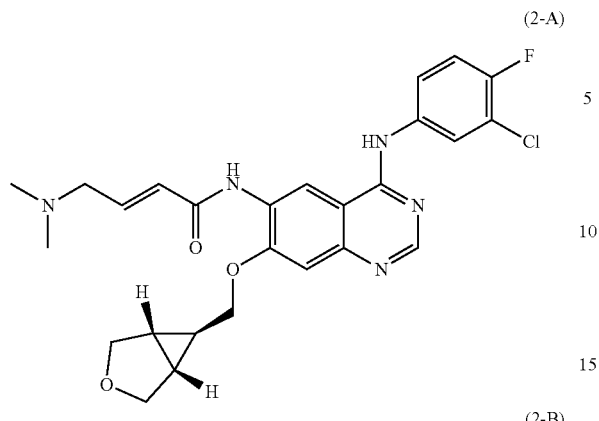

(2-B)

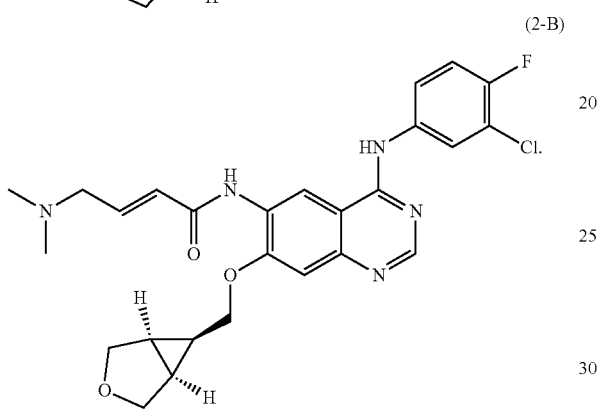

In some embodiments, provided is a compound obtained by following the synthetic and purification steps described in Example 2, or a salt, solvate, polymorph, metabolite or prodrug thereof.

In some embodiments, the compound is of the formula (I):

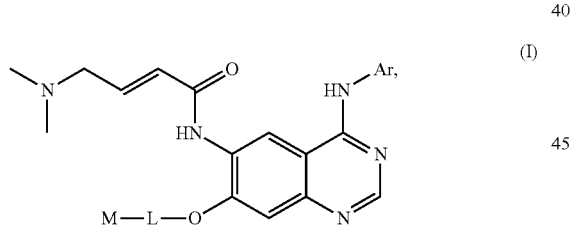

(I)

or a salt, solvate, polymorph, metabolite or prodrug thereof, wherein:

Ar is a substituted monocyclic phenyl or monocyclic heteroaryl, optionally substituted with 0-4 groups selected from halogen, trifluoromethyl, trifluomethoxy, $C_{1-3}$ alkyl, ethynyl, ethenyl, $C_{1-3}$ alkoxyl; or $O(CH_2)_n Ar^1$, where n is 0 or 1;

$Ar^1$ is selected from monocyclic aryl or 5-6 membered heteroaryl group, and the aryl or heteroaryl may be substituted with 0-3 groups selected from halogen, trifluoromethyl, trifluomethoxy, $C_{1-3}$ alkyl, $C_{2-3}$ alkynyl, $C_{2-3}$ alkenyl, and $C_{1-3}$ alkoxyl;

L is selected from $(CH_2)_m$, where m is 0 or 1;

M is a 6-10 membered bicyclic heterocycle, containing one or more O, N, or S atoms, and the heterocycle may be further substituted with one or more halogen, $C_{1-3}$ alkyl, hydroxyl, or $C_{1-3}$ alkoxyl.

Preferred examples of Ar in the formula (I) include, but are not limited to:

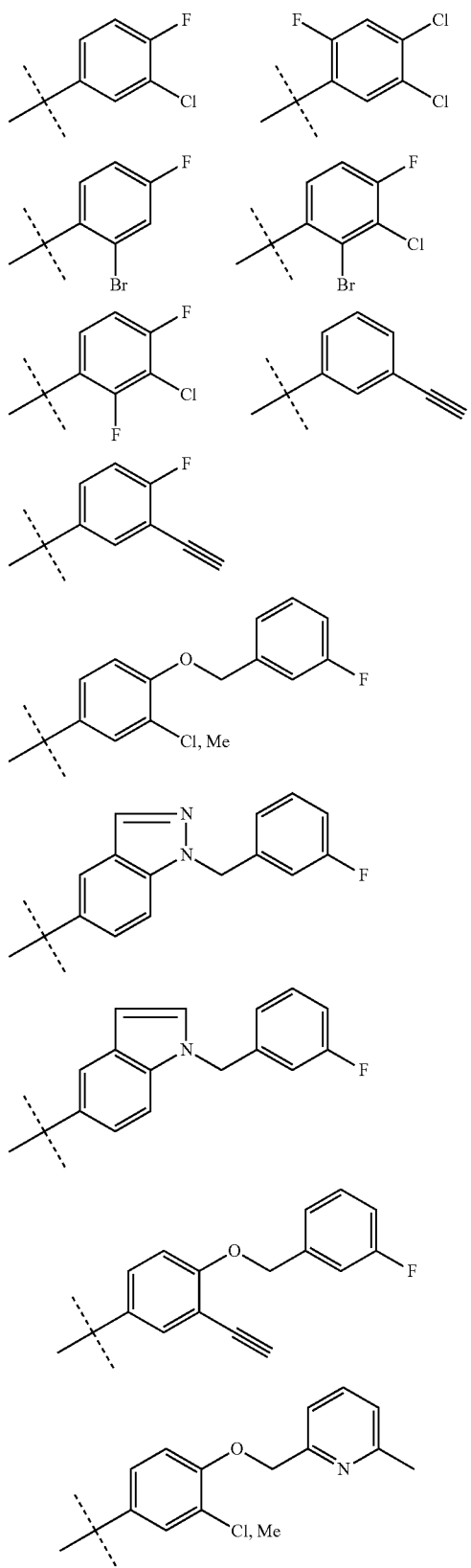

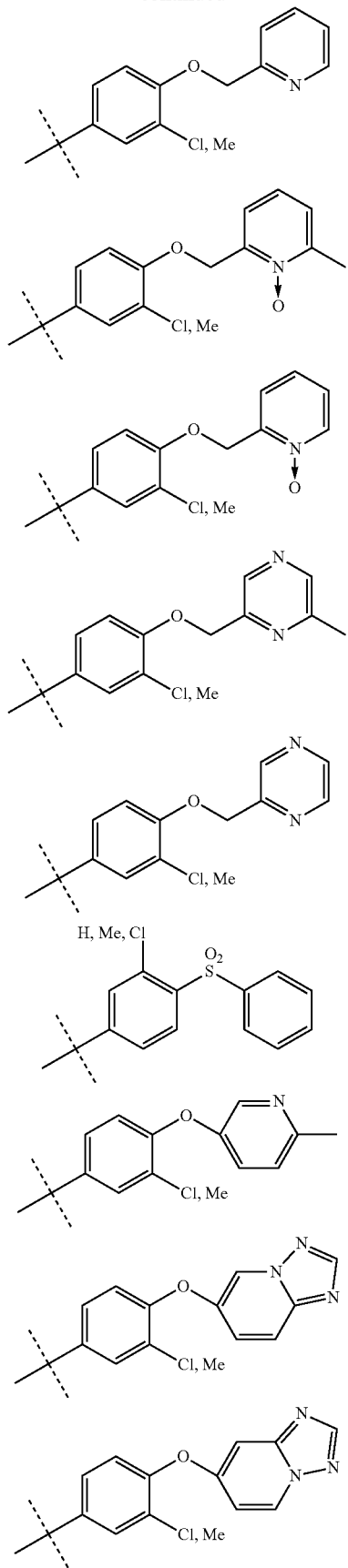

In some embodiments, the term "alkenyl" refers to linear or branched-chain hydrocarbon radical of two to twelve carbon atoms, containing at least one double bond, such as ethenyl, propenyl, and the like, wherein the alkenyl radical may be optionally substituted independently with one or more substituents described herein, and includes radicals having "cis" and "trans" orientations, or alternatively, "E" and "Z" orientations. The preferred alkenyl radicals are those with 2 to 6 carbon atoms ("$C_2$-$C_6$ alkenyl").

In some embodiments, the term "alkynyl" refers to a linear or branched hydrocarbon radical of two to twelve carbon atoms containing at least one triple bond. Examples include ethynyl, propynyl, and the like, wherein the alkynyl radical may be optionally substituted independently with one or more substituents described herein. Preferred alkynyl radicals are those having 2 to 6 carbon atoms ("$C_2$-$C_6$ alkynyl").

In some embodiments, an aryl is an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkyloxy, trifluoromethyl, aryl, heteroaryl, and hydroxy.

In some embodiments, a heteroaryl is a monocyclic aromatic radical of 5 to 10 ring atoms or a polycyclic aromatic radical, containing one to four ring heteroatoms selected from nitrogen, oxygen, or sulfur, the remaining ring atoms being carbon. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Other non-limiting examples of heteroaryl include [1,2,4]triazolo[1,5-a]pyridinyl, imidazo[1,2-a]pyridinyl and indazolyl.

In some embodiments, the term "heterocyclyl" refers to a saturated or partially unsaturated cyclic radical of 3 to 14 ring atoms in which at least one ring atom is a heteroatom selected from nitrogen, oxygen and sulfur, the remaining ring atoms being carbon where one or more ring atoms may be optionally substituted independently with one or more substituent described herein. The radical may be a carbon radical or heteroatom radical. "Heterocyclyl" also includes radicals where heterocycle radicals are fused with aromatic or heteroaromatic rings. A "heterocyclyl" may be mono-cyclic, bicyclic, multi-cyclic. Spiro moieties are also included within the scope of this definition. Examples of "heterocyclyl" include, but are not limited to, pyrrolidinyl, piperidinyl, piperazinyl, tetrahydrofuranyl, tetrahydropyranyl, morpholinyl, thiomorpholinyl, homopiperazinyl, phthalimidyl, 3-oxabicyclo[3.1.0]hexyl (e.g., 3-oxabicyclo[3.1.0]hexan-6-yl and 3-oxabicyclo[3.1.0]hexan-1-yl), and derivatives thereof.

Certain examples of compounds of the invention are listed in Table 1.

TABLE 1

| Entry No. | Structure | Name |
|---|---|---|
| 1 | 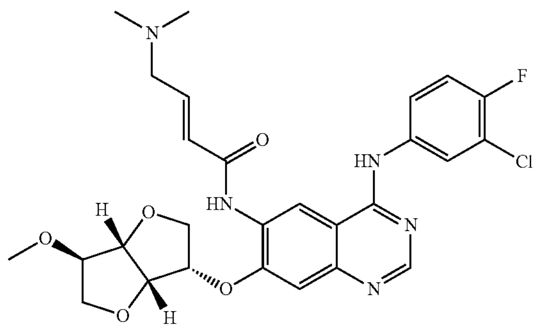 [SMILES: CO[C@@H]1CO[C@@H]2[C@H]1OC[C@@H]2Oc1cc2ncnc(Nc3ccc(F)c(Cl)c3)c2cc1NC(=O)/C=C/CN(C)C] | (E)-N-(7-((3R,3aS,6S,6aS)-hexahydro-3-methoxyfuro[3,2-b]furan-6-yloxy)-4-(3-chloro-4-fluorophenylamino)quinazolin-6-yl)-4-(dimethylamino)but-2-enamide |
| 2 | 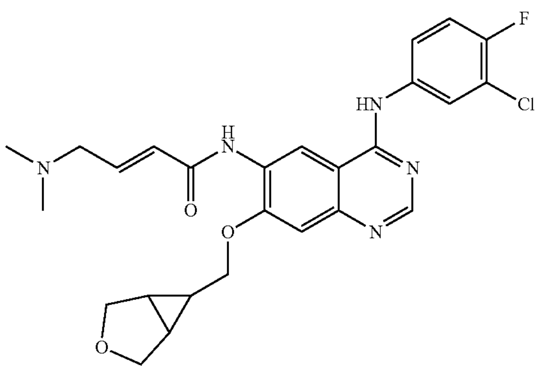 [SMILES: CN(C)C/C=C/C(=O)Nc1cc2c(Nc3ccc(F)c(Cl)c3)ncnc2cc1OCC1C2COCC21] | (E)-N-(7-((3-oxa-bicyclo[3.1.0]hexan-6-yl)methoxy)-4-(3-chloro-4-fluorophenylamino)quinazolin-6-yl)-4-(dimethylamino)but-2-enamide |
| 3 | 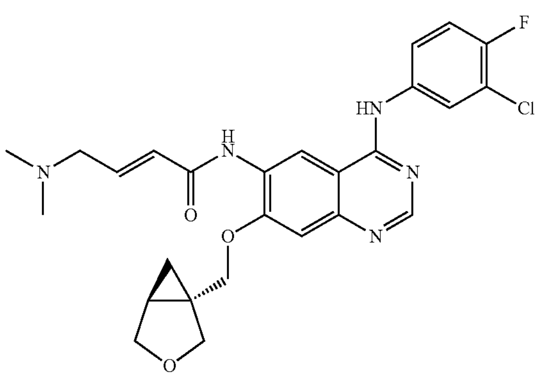 [SMILES: CN(C)C/C=C/C(=O)Nc1cc2c(Nc3ccc(F)c(Cl)c3)ncnc2cc1OC[C@]12COC[C@H]1C2] | (E)-N-(7-(((1S,5S)-3-oxa-bicyclo[3.1.0]hexan-1-yl)methoxy)-4-(3-chloro-4-fluorophenylamino)quinazolin-6-yl)-4-(dimethylamino)but-2-enamide |
| 4 | 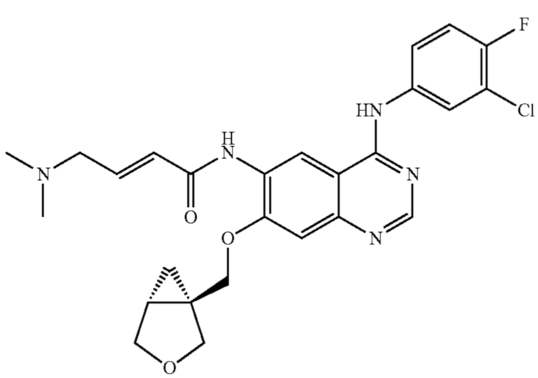 [SMILES: CN(C)C/C=C/C(=O)Nc1cc2c(Nc3ccc(F)c(Cl)c3)ncnc2cc1OC[C@@]12COC[C@@H]1C2] | (E)-N-(7-(((1R,5R)-3-oxa-bicyclo[3.1.0]hexan-1-yl)methoxy)-4-(3-chloro-4-fluorophenylamino)quinazolin-6-yl)-4-(dimethylamino)but-2-enamide |

TABLE 1-continued

| Entry No. | Structure | Name |
|---|---|---|
| 5 | 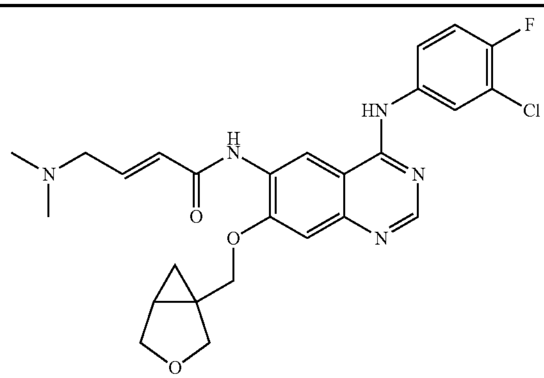 | (E)-N-(7-((3-oxa-bicyclo[3.1.0]hexan-1-yl)methoxy)-4-(3-chloro-4-fluorophenylamino)quinazolin-6-yl)-4-(dimethylamino)but-2-enamide |

Salts of these compounds can be formed with the acids including, but are not limited to, malic acid, lactic acid, maleic acid, fumaric acid, succinic acid, hydrochloric acid, methanesulfonic acid, toluenesulfonic acid, benzenesulfonic acid, sulfuric acid, phosphoric acid, citric acid, tartaric acid, acetic acid, propionic acid, caprylic acid, caproic acid, and benzoic acid.

Except as expressly defined otherwise, the described structures of this invention include all the isomeric forms (such as enantiomers, non-enantial isomers, geometric isomers, and stereoisomers (diasteromers)): such as (R)- or (S)-conformers from asymmetric centers, (Z) and (E)-isomers from double bond, and (Z) and (E) conformation isomers. Accordingly, single stereochemical isomers of the compounds of the invention or its enantiomer, non-enantial isomers, or mixture of geometric isomers (or conformers) all belong to the scope of this invention.

The compounds of the invention may contain asymmetric centers or chiral centers, therefore the existence of different stereoisomers. All stereoisomeric forms of compounds of the invention, including but not limited to, diastereomers, enantiomers, asymmetric rotamers and their mixtures, such as the racemic mixture, comprised part of this invention. Many organic compounds exist in optically active form, ie they have the ability to rotate the plane of plane polarized light. When the optical activities are described, prefix D, L or R, S are used to describe the absolute configuration. Prefixes d, l or (+), (−) are used to described the direction of rotation, with (−) or l indicating rotating left, and (+) or d for rotating right. Theses stereoisomers have the same two dimensional formula, but their three dimensional structures are different. Specific sterepisomers can be enantiomers (mirror image isomers), and the mixture of isomers is referred to mixture of enantiomers. A 50:50 mixture of enantiomers are referred to racemates. The term "racemate" refers to equal molar mixture of two optical enantiomers, and thus lacking optimal activity.

The term "tautomer" or "tautomeric form" used in this invention refers to that isomers of different energy can cross the low energy barrier and become exchangeable. For example, proton tautomers (proton migration) include the isomers resulting from proton migration, such as ketone-enol and imine-enamine isomers. Valence tautomers include isomers resulting from rearrangement of bond electrons.

Except as expressly defined otherwise, the compounds in this invention include all the tautomers.

Unless indicated otherwise, all stereo isomers, geometric isomers, tautomers, N-oxides, hydrates, solvates, metabolites, salts and pharmaceutically acceptable prodrugs of a compound of the invention are within the scope of the invention.

The term "prodrug" as used herein refers to a compound that may be converted in vivo to a compound of the formula (I). The conversion is affected by hydrolysis in blood or enzymatic conversion in blood or in tissue of the prodrug to the parent structure.

A "metabolite" is a product produced through metabolism in the body of a specified compound or its salt. Metabolites of a compound may be identified by using routine techniques known in the art and their activities determined using tests such as those described herein. Such products can be obtained from the parent compound via oxidation, reduction, hydrolysis, amidation, amide hydrolysis, esterification, ester hydrolysis, enzyme catalyzed fragmentation, etc. Accordingly, this invention includes all the metabolites of the compounds, and includes all the metabolites after the compounds are sufficiently exposed in mammals for a period of time.

"Pharmaceutically acceptable salts" in the invention refer to organic or inorganic of the compounds of this invention. Pharmaceutically acceptable salts are well known in the art.

Pharmaceutically acceptable salts formed from non-toxic acids include, but not limited to the salts formed from mineral acids reacting with an amino group, such as hydrochloric acid salt, hydrobromic acid salt, phosphoric acid salt, sulfuric acid salt, nitric acid salt; and with an organic acid such as acetic acid salt, oxalic acid salt, maleic acid salt, tartric acid salt, citric acid salt, succinic acid salt, malonic acid salt; or salts can also be prepared by alternative methods as described in literature, such as ion-exchange methods. Other pharmaceutically acceptable salts include Adipate, Alginate, ascorbate, aspartate, benzenesulfonate salt, benzoate salt, heavy sulfate, borate, butyrate, camphor, salts, camphor sulfonate, cyclopentyl C formategluconate, sodium dodecyl sulfate, ethylene sulfonate, formate, fumarate salts, glucoheptonate salts, glycerol phosphate, gluconate, semi-sulfate, heptanoic acid salts, caproic acids alt, iodate2-hydroxyethylsulfonate, lactobionate, lactate, laurate, lauryl sulfate, malate, malonate, methanesulfonate, 2-naphthalenesulfonate, nicotinate, nitrate, oleate, palmitic acid salt, pamoic acid salt, pectic acid salts, persulfate salts, 3-phenylpropionate, picrate, pentyl formate, propionate, stearate, thiocyanate, tosylate, undecanoate, valerate, etc. Salts prepared from reaction with an appropriate base include alkaline, alkaline earth metal, ammonium, and $N^+(C_1-C_4Alkyl)_4$. This invention also include any quarternary salt from compounds containing an "N" group, water soluble or lipid soluble or suspension can also be obtained via quaternary ammonium method. Alkaline and alkaline earth metal salts include sodium, lithium, potassium, calcium, magnesium, etc. Pharmaceutically acceptable salts further include appropriate harmless ammonium, quaternary ammonium, and ions to counter ammonium cations such as halide, hydroxide, carboxylate, sulfate, phosphate, $C_1$-$C_3$ alkanesulfate and arylsulfate.

Specifically, the salt is a pharmaceutically acceptable salt. The term "pharmaceutically acceptable" includes the substance or composition that must be suitable chemically or toxicologically to form formulation with other components of the preparation and to treat mammals.

When a compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha-hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

When a compound of the invention is an acid, the desired pharmaceutically acceptable salt may be prepared by any suitable method, such as an inorganic or organic base, such as an amine (primary, secondary or tertiary), an alkali metal hydroxide or alkaline earth metal hydroxide, or the like. Suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The term "solvate" refers to an aggregate of a compound of this invention with one or more solvent molecules. Solvents that form solvate include, but not limited to, water, isopropanol, ethanol, methanol, methyl sulfoxide, ethyl acetate, acetic acid, aminoethanol. The term "hydrate" refers to an aggregate formed with water as solvent molecules.

The compounds in the invention exist as parent forms, or appropriate pharmacetutically acceptable derivatives. Based on this invention, the pharmacetutically acceptable derivatives include, but not limited to pharmacetutically acceptable prodrugs, salts, esters, salts of esters, or other derivatives or compositions prepared based directly or indirectly on the needs of patients, or otherwise described compounds in this invention or their metabolites, or other degradation products.

Synthesis

In one aspect, provided is a method for making a compound of the formula (I):

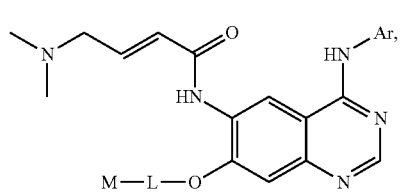

(I)

wherein:

Ar is a monocyclic aryl or monocyclic heteroaryl, optionally substituted with 0 to 4 substituents independently selected from the group consisting of halogen, trifluoromethyl, trifluoromethoxy, $C_1$-$C_3$ alkyl, ethynyl, ethenyl, $C_1$-$C_3$ alkoxy, —O(CH$_2$)$_n$Ar$^1$; —(CH$_2$)$_m$Ar$^2$ and —S(O)$_2$Ar$^3$;

m and n are independently 0 or 1;

each Ar$^1$, Ar$^2$ and Ar$^3$ is independently a monocyclic aryl or 5 or 6 membered heteroaryl, where each aryl or heteroaryl is optionally substituted with 0 to 3 substituents independently selected from the group consisting of halogen, trifluoromethyl, trifluoromethoxy, $C_1$-$C_3$ alkyl, $C_2$-$C_3$ alkynyl, $C_2$-$C_3$ alkenyl and $C_1$-$C_3$ alkoxy;

L is a bond or CH$_2$; and

M is a 6-10 membered bicyclic heterocycle containing one or more annular heteroatoms independently selected from O, N and S, optionally substituted with one or more substituents independently selected from the group consisting of halogen, $C_1$-$C_3$ alkyl, hydroxyl and $C_1$-$C_3$ alkoxy, comprising the steps of:

Step 1: reacting compound of formula (Ia):

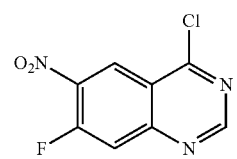

Ia with a compound of formula ArNH$_2$ to obtain a compound of the formula (Ib):

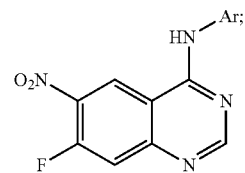

Ib

Step 2: treating an alcohol of the formula M-L-OH with a strong base, and then adding the compound of the formula (Ib) to obtain a compound of the formula (Ic):

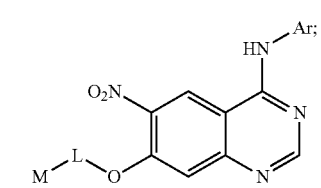

Ic

Step 3: reducing the compound of the formula (Ic) to produce a compound of the formula (Id):

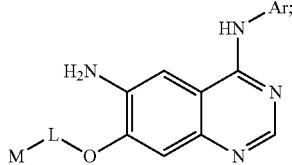

Step 4: coupling the compound of the formula (Id) with an acid of the formula (Ie):

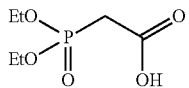

using a coupling reagent to form an amide of the formula (If):

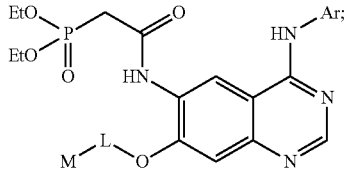

and

Step 5: producing a compound of the formula (I) by a Wittig reaction of the compound of the formula (If) with 2-dimethylaminoacetaldehyde.

In some embodiments, provided is a method for making a compound of the formula (I) comprising performing the synthetic steps shown in Scheme 1:

Scheme 1

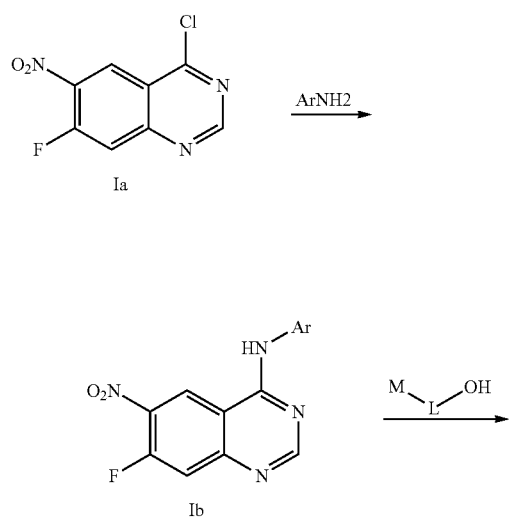

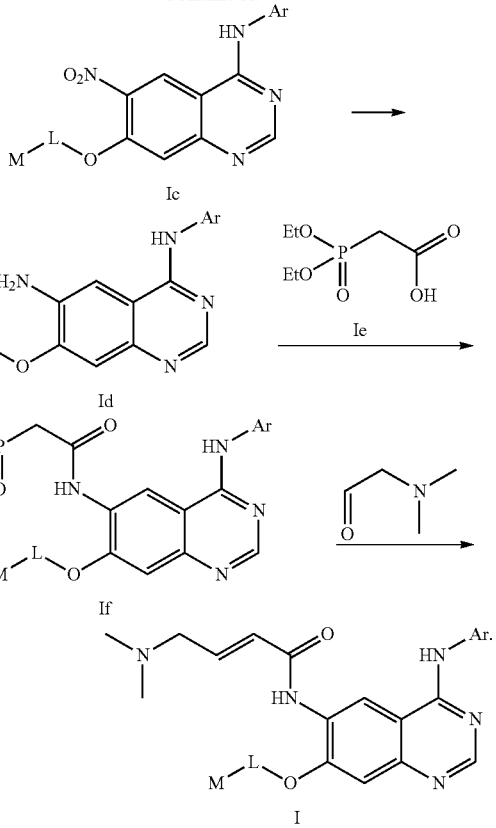

In some embodiments, 4-Chloroquinazoline Ia (reference: Rewcastle, G. W., et al. J. Med. Chem., 1996, vol. 39, 918-928) is reacted with an aniline compound to give compound Ib. The corresponding alcohol M-L-OH is treated with a strong base (sodium hydride), and to it is added compound Ib. The resulted compound Ic is reduced to amine Id. The reduction method can be platinum-carbon catalyzed hydrogenation, or iron powder in acid. The amine Id prepared by this method formed amide with a coupling agent such as CDI (N,N'-carboyldiimidazole) and acid Ie to give a compound If. Wittig reaction of compound If with freshly prepared 2-dimethylaminoacetaldehyde affords a compound of general Formula (I).

In some embodiments, provided is a method for making a compound of formula (I), comprising the steps described above, wherein:

Ar is a substituted monocyclic phenyl or monocyclic heteroaryl, optionally substituted with 0-4 groups selected from halogen, trifluoromethyl, trifluoromethoxy, $C_{1-3}$ alkyl, ethynyl, ethenyl, $C_{1-3}$ alkoxyl; or $O(CH_2)_n Ar^1$, where n is 0 or 1;

$Ar^1$ is selected from monocyclic aryl or 5-6 membered heteroaryl group, and the aryl or heteroaryl may be substituted with 0-3 groups selected from halogen, trifluoromethyl, trifluomethoxy, $C_{1-3}$ alkyl, $C_{2-3}$ alkynyl, $C_{2-3}$ alkenyl, and $C_{1-3}$ alkoxyl;

L is selected from a bond or $CH_2$;

M is a 6-10 membered bicyclic heterocycle, containing one or more O, N, or S atoms, and the heterocycle may be further substituted with one or more halogen, $C_{1-3}$ alkyl, hydroxyl, or $C_{1-3}$ alkoxyl.

As a preferred embodiment, the strong base in step 2 is sodium hydride; and as another preferred embodiment, the reduction in step 3 is carried out with platinum-carbon catalyzed hydrogenation, or iron powder-acid reduction.

Methods of Treatment

In another aspect, provided is method for treating a receptor protein tyrosine kinase-related disease in an individual in need thereof comprising administering to the individual an effective amount of a compound of the formula (I), or any variation thereof described herein, such as a compound listed in Table 1 and in the Examples 1-5 (e.g., NT112), or a salt, solvate, polymorph, metabolite or prodrug thereof. In some embodiments, the receptor protein tyrosine kinase-related disease is a cancer selected from the group consisting of breast cancer, colorectal cancer, lung cancer, papillary carcinoma, prostate cancer, lymphoma, colonpancreatic cancer, ovarian cancer, cervical cancer, central nervous system cancer, osteogenic sarcoma, kidney cancer, liver cancer, bladder cancer, gastric cancer, head and neck squamous cell carcinoma, melanoma and leukemia. In some embodiments, the cancer is a breast cancer, gastric cancer, lung cancer, colorectal cancer, central nervous system cancer, or head and neck squamous cell carcinoma. In some embodiments, the cancer is an erlotinib-resistant cancer (e.g., an erlotinib-resistant non-small cell lung cancer).

In some embodiments, "treatment" or "treating" is intended to mean at least the mitigation of a disease condition in a mammal, such as a human, that is affected, at least in part, by the activity of one or more receptor protein tyrosine kinases, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In some embodiments, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

In some embodiments, the term "individual" as used herein refers to a mammal, including but not limited to, bovine, horse, feline, rabbit, canine, rodent, or primate (e.g., human). In some embodiments, an individual is a human. In some embodiments, an individual is a non-human primate such as chimpanzees and other apes and monkey species. In some embodiments, an individual is a farm animal such as cattle, horses, sheep, goats and swine; pets such as rabbits, dogs and cats; laboratory animals including rodents, such as rats, mice, and guinea pigs; and the like. The invention may find use in both human medicine and in the veterinary context. In some embodiments, the individual is suffering from a receptor protein tyrosine kinase-related disease (e.g., cancer), or has been diagnosed to have a receptor protein tyrosine kinase-related disease (e.g., cancer).

In one embodiment, the invention provides a pharmaceutical composition, containing a compound of Formula (I), or its pharmaceutically acceptable salts or prodrugs and pharmaceutically acceptable carriers or excipients, and the preparation of drugs to treat receptor tyrosine kinase related diseases or inhibitors of receptor tyrosine kinases, especially application of erbB family receptor tyrosine kinase inhibitors.

Also provided is a method for modulating receptor protein tyrosine kinases (RTKs), including the binding of RTK with a compound of formula (I) or a pharmaceutically acceptable salt thereof.

Further provided is a method of applying compounds or its pharmaceutical composition to treat diseases related to receptor tyrosine protein kinases, including giving patients the appropriate doses of these compounds or the pharmaceutical composition containing these compounds.

Therapeutically effective amounts of the compounds of the invention may be used to treat diseases mediated by modulation or regulation of receptor protein tyrosine kinases (RTKs). An "effective amount" is intended to mean that amount of compound that, when administered to a mammal in need of such treatment, is sufficient to effect treatment for a disease mediated by the activity of one or more RTKs. Thus, for example, a therapeutically effective amount of a compound of the formula (I), or a salt, active metabolite or prodrug thereof, is a quantity sufficient to modulate, regulate, or inhibit the activity of one or more RTKs such that a disease condition which is mediated by that activity is reduced or alleviated. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of this invention, an effective dosage of drug, compound, or pharmaceutical composition is an amount sufficient to accomplish prophylactic or therapeutic treatment either directly or indirectly.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art.

Compounds of this invention has shown superior pharmacokinetic properties compared to a known standard compound afatinib. Higher oral bioavailability and better PK profile may translate to a lower dose to achieve the same efficacy; and potentially lower side effect as a smaller dose is required.

In order to use a compound of the formula (I), or a pharmaceutically acceptable salt or in vivo cleavable prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the formula (I), or a pharmaceutically acceptable salt or in vivo cleavable prodrug thereof, as defined hereinbefore in association with a pharmaceutically acceptable diluent or carrier.

The compounds of the invention are administered either singly or in combination to a mammal to treat a receptor protein tyrosine kinase-related disease, such as various types of cancer, e.g., cancer of the colon, ovary, bladder, stomach, lung, uterus, and prostate. The compound may be administered via any acceptable route, e.g., intra venous, oral, intra muscular, via suppository, etc. The compounds can be formulated as oral dosage forms, e.g., tablets, capsules, liquid suspension, etc, as suppositories, or may be prepared as a liquid for injection, for example. The skilled practitioner can select the appropriate route and dosage amount for treatment of the specific receptor protein tyrosine kinase-related disease to be treated.

Formulations

"Pharmaceutical composition" is a mixture of one or more compounds of this invention or their pharmaceutically acceptable salts or prodrugs with other compounds, other components are physiologically or pharmaceutically acceptable carriers or excipients. The purpose of a pharmaceutical composition is to facilitate administration of the compound to a living thing.

As described in this invention, a pharmaceutically acceptable composition in the present invention further contains a pharmaceutically acceptable carrier, adjuvant, or excipient, as in the application of the present invention, including any solvent, diluents, or other liquid excipients, dispersing agent or suspending agent, surfactants, isotonic agents, thickeners, emulsifiers, preservatives, solid binders or lubricants, etc., suitable for specific target formulations A pharmaceutically acceptable carrier includes, but is not limited to, ion exchange agents, aluminum, aluminum stearate, lecithin, serum proteins, such as human serum protein, buffers, such as phosphate, glycine, sorbic acid, potassium sorbate, saturated vegetable oil and partial glycerol ester mixture, water, salt or electrolyte, protamine sulfate, disodium hydrogen phosphate, potassium hydrogen phosphate, sodium chloride, zinc salts, colloidal silica, magnesium trisilicate, polyvinyl pyrrolidone, polyacrylic acid lipid, wax, polyethylene-polyoxypropylene-blocking polymer, lanolin, sugar, lactose, glucose and sucrose; Starch such as corn starch and potato starch; cellulose and its derivatives such as sodium carboxymethyl cellulose, ethyl cellulose and cellulose acetate; tree wax powder; malt; gelatin; talc; excipients such as cocoa bean butter and suppository waxtilting; Oils such as peanut oil, cottonseed oil, safflower oil, sesame oil, olive oil, corn oil and soybean oil; diols such as propylene glycol and polyethylene glycol; esters such as ethyl oleate and ethyl laurate; agar; buffering agent such as magnesium hydroxide and aluminum hydroxide; alginate; pyrogen water; isotonic saline; Stringer solution; ethanol, phosphate buffer solution, and other non-toxic suitable lubricant, such as baysodium sulfate and magnesium stearate, coloring agents, release agents, coating agent, sweeteners, flavoring agents and spices, preservatives and antioxidants.

The compositions of the invention may be in a form suitable for oral use, for injection, for inhalation, for topical use, for rectal dosing, for administration by insufflations, for sublingual use, for vaginal dosing, or for implant use. The term "for injection" refers to subcutaneous, intravenous, intramuscular, joint, intra-synovial membrane (cavity), intra-sternum, intra-membrane, intraocular, intrahepatic, intralesional and intracranial injection or infusion technology, preferred composition is for oral use, intraperitoneal use, and for intravenous injection. Sterile injection of the composition of this invention can be water or oily suspensions. These suspensions can be prepared with publicly known technology using suitable formula of dispersing agents, wetting agents and suspending agent. Sterile injection can be a sterile solution or suspension of non-toxic acceptable diluent or solvent, such as 1,3-butanediol. The acceptable excipient and solvents can be water, Ringer solution, and isotonic sodium chloride solution. Furthermore, sterile non volatile oil can be used solvent or suspension medium, according to the prior art.

For this purpose, any mild, non-volatile oil may be the synthetic mono or diacylglycerol. Fatty acids such as oleic acid and its glyceride derivatives can be used for the preparation of the intravenous injectable, natural pharmaceutically acceptable oils, such as olive oil or castor oil, especially their polyoxyethylene derivatives can also be used. These oil solutions or suspensions can contain long-chain alcohol diluent or dispersant such as carboxymethyl cellulose or similar dispersing agents; pharmaceutical acceptable dosage forms include emulsions and suspensions. Other commonly used surfactants, such as Tween, Span class, and other emulsifiers or biological drug efficiency enhancer, pharmaceutically acceptable solid, liquid, or other dosage forms can be applied to the target pharmaceutical preparation.

The pharmaceutically acceptable composition of the present invention can be an acceptable oral formulation for oral administration, including but not limited to, capsules, tablets, water suspension or solution. For oral tablets, carriers generally include lactose and corn starch. Lubricants such as magnesium stearate, are typically added. For oral capsule administration, suitable diluents include lactose and dried corn starch. When oral formulation is a water suspension, the active ingredients can be comprised of emulsifier and suspending agent. For these formulations, sweeteners, flavoring agents or colorants can be added.

In addition, the pharmaceutically acceptable compositions of the present invention can be in the form of a rectal suppository. These can be prepared by mixing the agent with the appropriate non-perfusion adjuvant. The mixture prepared this way is a solid at room temperature, but it become a liquid at rectal temperature and releases the drug in the rectum. Such substances include cocoa fat, beeswax, and polyethylene glycol. The pharmaceutically acceptable compositions of the present invention can be used for localized drug delivery, especially when treatment goal is easier to reach with topical drug delivery on certain treatment region or organs, such as disease of eye, skin or intestine. Suitable topical formulations can be prepared and applied to these areas or organs.

Rectal suppositories (see above) or a suitable enema can be applied to the local administration of the lower intestinal tract. Local skin spots can also be medicated the same way. For local administration, the pharmaceutically acceptable compositions can be prepared accordingly into a suitable ointment, the ointment containing the active ingredient suspended in or dissolved in one or more carriers. Localized drug delivery carriers of this invention include, but are not limited to mineral oil, liquid paraffin, white petrolatum, propylene glycol, polyoxyethylene, polyoxypropylene compound, emulsified wax and water. In addition, the pharmaceutically acceptable compositions can be prepared into a suitable lotion or cream, the lotion or cream containing the active ingredient is suspended in or dissolve in one or more pharmaceutically acceptable carriers. A suitable carrier, including, but not limited to, mineral oil, Span 60 (sorbitan monostearate), Tween 60 (polysorbate 60), cetyl ester wax, palm alcohol, 2-octyl dodecanol, benzyl alcohol and water.

A pharmaceutically acceptable composition for eye application can be prepared into formulations such as particulate suspensions in isotonic, pH adjusted sterile saline or other aqueous solutions, preferably isotonic solution and pH adjusted sterile saline or other aqueous solutions. The disinfection of preservatives such as benzalkonium chloride can be added to the formulation. In addition, the pharmaceutically acceptable compositions for the eye can be prepared into the ointment such as Vaseline. Administration of a pharmaceutically acceptable composition of the present invention can be applied via the gas solvents or inhalants thorough nose. This composition can be prepared from known formula and technology, or can be prepared as a salt solution using benzyl alcohol or other suitable preservatives, absorption enhancers, fluorocarbons, or other conventional solubilizing agent or dispersing agent to improve the bioavailability.

Liquid formulations for oral administration include, but not limited to, pharmaceutically acceptable emulsions, micro-emulsion, solution, suspension, syrup and elixir. In addition to the active compounds, the liquid dosage forms may contain inert diluents known in the art, for example, water or other solvent, solubilizer and emulsifier, such as ethanol, isopropanol, ethyl carbonate, ethyl acetate, benzyl alcohol, benzyl benzoate, propylene glycol, 1,3-butanediol, dimethylformamide, oils and fats (in particular, cottonseed, groundnut, corn, microbes, olive, castor and sesame oil), glycerin, 2-tetrahydrofuranmethanol, polyethyleneglycol, dehydrated sorbitol fatty acid esters, and their mixtures. Addition to inert diluents, the oral compositions can also contain adjuvants such as wetting agents, emulsifiers or suspending agent, sweeteners, flavorings and fragrances.

The solid dosage forms for oral administration include capsules, tablets, pills, powders and granules. In these formulations, the active compounds are mixed with at least one pharmaceutically acceptable inert excipients or carrier, such as sodium citrate or calcium phosphate or filling agents, or (a) fillers such as starch, lactose, sucrose, glucose, mannitol and silicic acid; (b) adhesives such as carboxymethylcellulose, alginates, gelatin, polyethylene pyrrole ketone, sucrose and gum arabic; (c) moisturizing agents such as glycerol; (d) disintegrating agents such as agar, calcium carbonate, potato starch or tapioca starch, alginic acid, certain silicates and sodium carbonate; (e) blocker solution, such as paraffin; (f) absorption promoter such as quaternary ammonium compounds; (g) wetting agents such as decahexanyl alcohol and glycerol monostearate; (h) absorbents such as kaolin and bentonite, (i) lubricants such as talc, calcium stearate, magnesium stearate, solid polyethylene glycol, laurylsodium sulfate, and mixtures thereof. Formulations such as capsules, tablets and pills can contain buffer.

Injection, such as sterile injection or oily suspensions can be prepared by well known technology using suitable dispersing agents, wetting agents and suspending agent. Sterile injection can be prepared at the location of application by a non-toxic locally acceptable diluent or solvent to give sterile injection, suspension or emulsion, for example, 1,3-butanediol solution. Acceptable excipients and solvents are water, Ringer's solution, USP and isotonic sodium chloride solution. In addition, sterile, non-volatile oil has been used as the solvent or suspension medium. Any mild, non-volatile oil used for this purpose may include the synthetic mono or di-glucosyl diacylglycerol. In addition, fatty acids such as oleic acid can be used in injection.

Injection can be sterile, such as filtration through a sterilization filter, or incorporation of a sterilizing agent in the form of sterile solid compositions. Sterilizing agent can be dissolved in or dispersed in sterile water or sterile injection medium prior to use. In order to prolong the effect of the compounds of the invention, subcutaneous or intramuscular injection can be used to slow the absorption of compounds. The problem of poor water solubility of the crystal or non-crystalline material can be solved by using liquid suspension. The absorption rate of the compound depends on its dissolution, in turn depends on grain size and crystal shape. In addition, the compound is dissolved or dispersed in the oil excipient to delay absorption of the compound injection.

Preferably, the compounds of the invention are formulated into unit dosage forms in order to reduce the amount of drug administered and to obtain dose uniformity. The term "unit dosage form" as used herein refers to physical drug dispersion unit that patients will receive for the appropriate treatment. However, the total daily dosage of the compounds or compositions of the present invention will be determined by the physician based on the reliable range of medical judgment. The specific effective dose level for a particular patient or organism will depend on many factors, including the disease or condition treated and the severity of the disease or condition, the activity of specific compounds, the specific composition, the patient's age, body weight, health status, gender, dietary habits, time of administration, route of administration and excretion rate of the specific compound used, the duration of treatment, drug combination or drug used in tandem with another specific compounds, as well as some other pharmacological factors known in the art.

EXAMPLES

The following specific examples further illustrate the present invention. However, it is well understood that the examples below are intended to illustrate embodiments of the invention, and are not intended to limit the scope of the specification or claims in any way. Compounds of the invention can be prepared following the methods described herein or methods known in the art.

The structures of compounds are determined by nuclear magnetic resonance (NMR) and mass spectroscopy (MS). NMR shift (δ) has units of parts-per-million (ppm). NMR spectra were measured using a Bruker-300 NMR spectrometer. MS spectra were taken on an Agilent LC-MS (ESI+) mass spectrometer.

Unless otherwise specified, the reactions are carried out under nitrogen atmosphere.

Column chromatography and preparative thin layer chromatography were done using silica or thin-layer-silica plate manufactured by Merck.

Example 1

Preparation of (E)-N-(4-((3-chloro-4-fluorophenyl)-7-(((3S,3aS,6R,6aS)-6-methoxyhexahydrofuro[3,2-b]furan-3-yl)oxy)quinazolin-6-yl)-4-(dimethylamino) but-2-enamide (1)

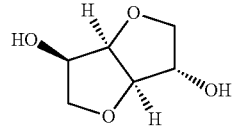

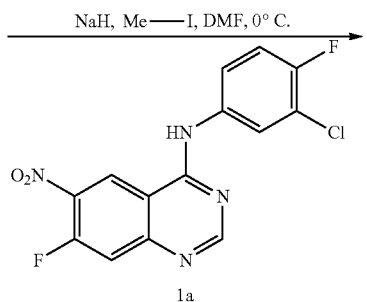

1a

-continued
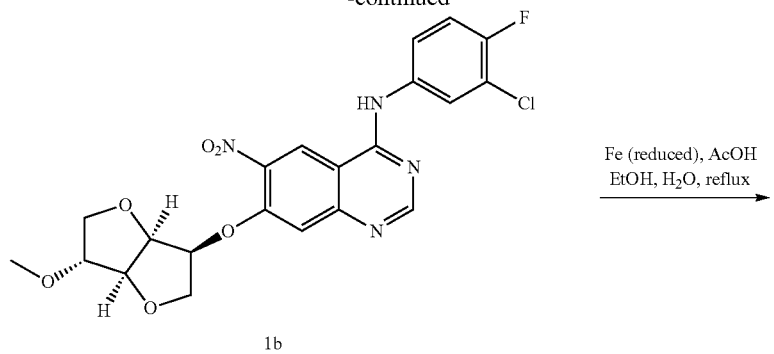
1b
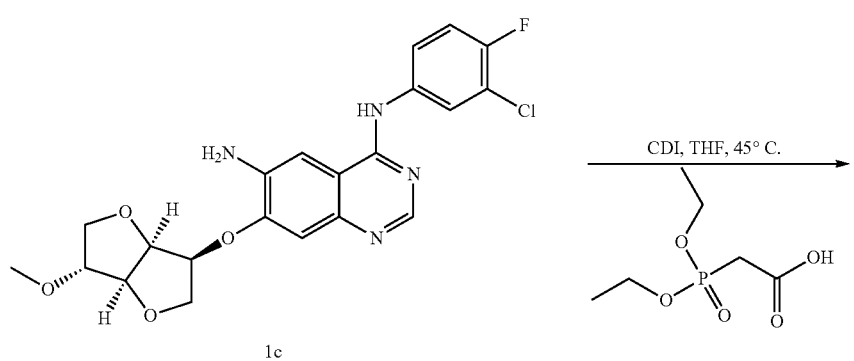
1c
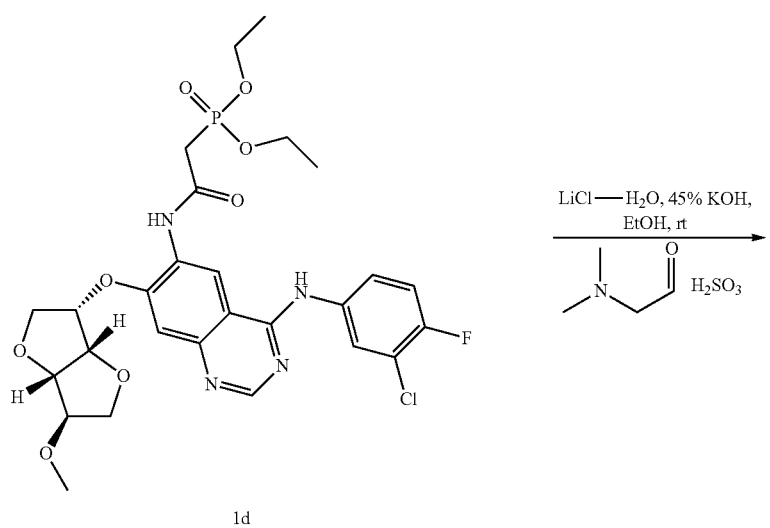
1d
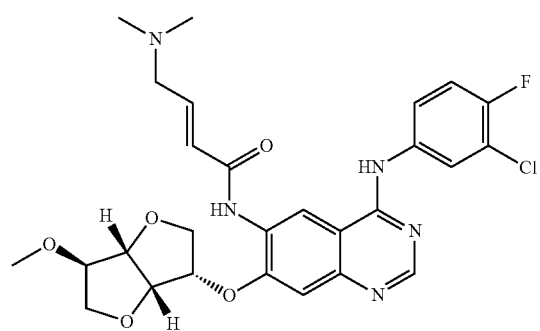 [SMILES: CO[C@@H]1CO[C@@H]2[C@H]1OC[C@@H]2Oc1cc2ncnc(Nc3ccc(F)c(Cl)c3)c2cc1NC(=O)/C=C/CN(C)C]
1

Step 1: preparation of N-(3-chloro-4-fluorophenyl)-7-(((3S,3aS,6R,6aS)-6-methoxyhexahydrofuro[3,2-b]furan-3-yl)oxy)-6-nitroquinazolin-4-amine (1b)

NaH (60% dispersion in mineral oil, 493 mg, 12.32 mmol) was added in portions to a stirring solution of dianhydro-D-glucitol (1.5 g, 10.26 mmol) in DMF (20 mL) at room temperature under $N_2$ (g) atmosphere. After 20 min, methyl iodide (639 μL, 10.26 mmol) was added, the mixture stirred for 30 min, cooled to 0° C., followed by stepwise addition of DMF (20 mL) and NaH (493 mg, 12.32 mmol). N-(3-chloro-4-fluorophenyl)-7-fluoro-6-nitroquinazolin-4-amine 1a (500 mg, 1.48 mmol, prepared according to Smaill, J. B., et al., Journal of Medicinal Chemistry, 2000, 43, 1380-1397) was added after 20 min and the reaction was quenched 30 min later at 0° C. by a slow addition of saturated $NH_4Cl$, followed by extraction with EtOAc (100 mL). The organic layer was washed with $H_2O$ (2×100 mL), brine (100 mL), dried over $MgSO_4$, and concentrated to a yellow residue 1b. MS m/z (ESI+), 477 [M+1].

Step 2: preparation of $N^4$-(3-chloro-4-fluorophenyl)-7-(((3S,3aS,6R,6aS)-6-methoxyhexahydrofuro[3,2-b]furan-3-yl)oxy)-6-nitroquinazoline-4,6-diamine (1c)

Glacial acetic acid (3 mL) was added to a stirring solution of 1b (700 mg, 1.47 mmol) in EtOH:$H_2O$ (90 mL, 2:1 (v/v)), followed by reduced iron (328 mg, 5.87 mmol). The mixture was refluxed for 1 hr and cooled to room temperature. 5M NaOH was added to adjust the pH to 7-8, diluted with EtOAc (100 mL), stirred vigorously for 30 min, and filtered through celite. The black cake was washed with warm EtOAc (2×100 mL) and the filtrates concentrated. The residue was diluted in $H_2O$ (100 mL), extracted with MeOH:DCM (2×100 mL, 1:9 (v/v)), the organic layer was washed with brine (100 mL), dried over $MgSO_4$, and concentrated to a yellow green residue (1c). LCMS m/z (ESI+): 447 [M+1].

Step 3: preparation of Diethyl(2-((4-(3-chloro-4-fluorophenyl)-7-(((3S,3aS,6R,6aS)-6-methoxyhexahydrofuro[3,2-b]furan-3-yl)oxy)quinazolin-6-yl)amino-2-oxoethyl)phosphonate (1d)

1,1-Carbonyldiimidazole (CDI, 310 mg, 1.91 mmol) and diethylphosphonoacetic acid (375 mg, 1.91 mmol) in THF (10 mL) were stirred at 40° C. for 30 min. A solution of 1c (657 mg, 1.47 mmol) in THF (3 mL) was added and the mixture stirred at 45° C. overnight. Once concentrated, the residue was diluted in EtOAc (100 mL), washed with sat. $NaHCO_3$ (50 mL), $H_2O$ (100 mL), brine (100 mL), dried over $MgSO_4$, and concentrated. The gray solid was sonicated in ether (30 mL), filtered and dried in vacuo. The resulting reside 1d was used for the synthesis of 1 without further purification. LCMS m/z (ESI+): 625 [M+1].

Step 4: preparation of (E)-N-(4-((3-chloro-4-fluorophenyl)-7-(((3S,3aS,6R,6aS)-6-methoxyhexahydrofuro[3,2-b]furan-3-yl)oxy)quinazolin-6-yl)-4-(dimethylamino)but-2-enamide 1

Lithium chloride monohydrate (105 mg, 1.28 mmol) was added to a solution of 1d (400 mg, 0.64 mmol) in EtOH (10 mL), followed by KOH (45% (wt), 1 mL) at room temperature. After 5 min, a solution of dimethylaminoacetaldehyde-hydrogen sulphite adduct (214 mg, 1.28 mmol, prepared according to method in WO2007/85638) in $H_2O$ (4 mL) was added, stirred for 15 min, concentrated, diluted in DCM (200 mL), washed with $H_2O$ (2×100 mL), brine (100 mL), dried over $MgSO_4$, and concentrated. Column chromatography (0-20% MeOH/DCM, gradient), followed by lyophilization afforded 1 as white solids (246 mg, 68.9%). $^1$HNMR (CDCl$_3$, 300 MHz) δ 9.16 (s, 1H), 8.66 (s, 1H), 8.04 (s, 1H), 7.90 (d, 1H), 7.75 (s, 1H), 7.56 (m, 1H), 7.40 (s, 1H), 7.17 (m, 1H), 7.06 (m, 1H), 6.25 (d, 1H), 5.05 (s, 1H), 4.85 (t, 1H), 4.74 (d, 1H), 4.32 (m, 2H), 4.01 (m, 2H), 3.78 (t, 1H), 3.54 (s, 2H), 3.20 (d, 2H), 2.35 (s, 6H). LCMS (ESI) m/z=559 (MH$^+$).

Example 2

Preparation of (E)-N-(7-((3-oxabicyclo[3.1.0]hexan-6-ylmethoxy)-4-((3-chloro-4-fluorophenyl)amino)quinazolin-6-yl)-4-(dimethylamino)but-2-enamide (2)

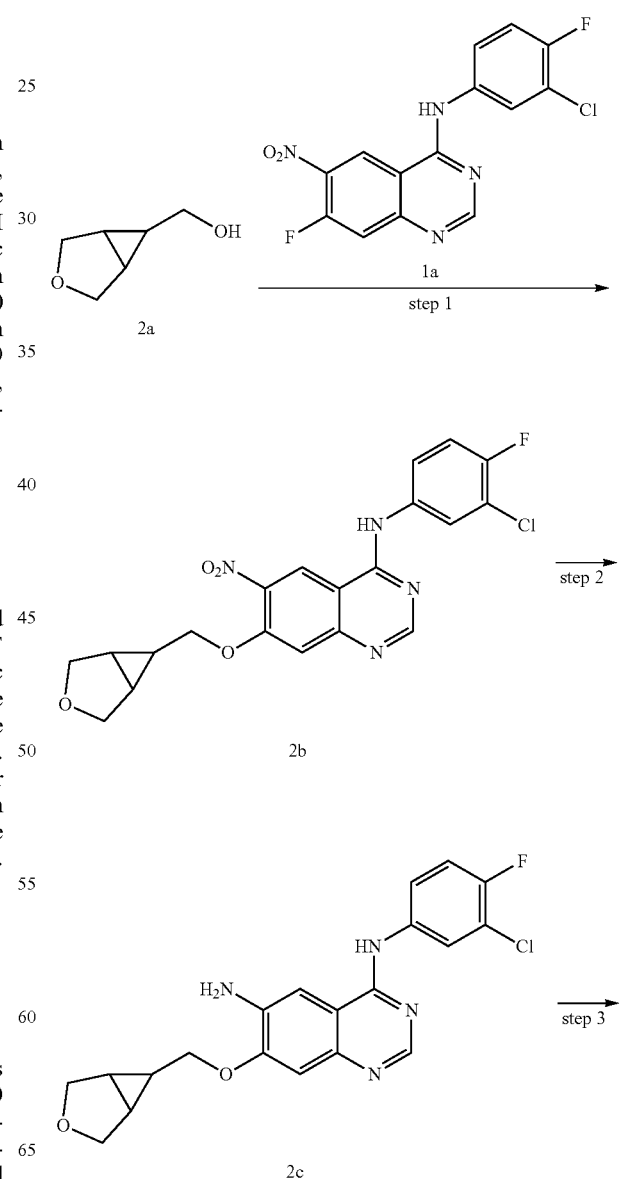

-continued

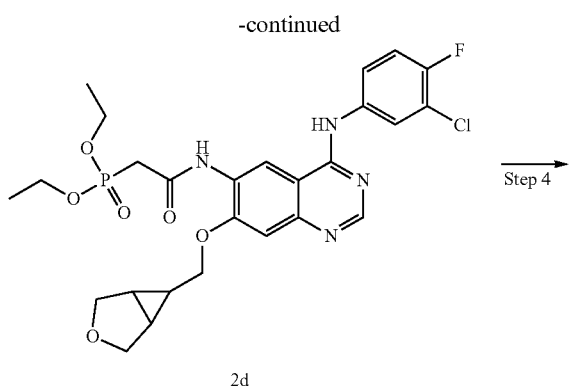

Step 1: preparation of 7-((3-oxabicyclo[3.1.0]hexan-6-ylmethoxy)-N-(3-chloro-4-fluorophenyl)-6-nitro-quinazolin-4-amine (2b)

NaH (60% dispersion in mineral oil, 480 mg, 12.0 mmol) was added in portions to a stirring solution of (3-oxa-bicyclo[3.1.0]hexan-6-yl)methanol (570 mg, 5.0 mmol; prepared according to procedures described in WO2012/021591A1) in DMF (40 mL) at room temperature under $N_2$ (g) atmosphere. After 20 min, the mixture was cooled to 0° C., followed by addition N-(3-chloro-4-fluorophenyl)-7-fluoro-6-nitro-quinazolin-4-amine 1a (1.54 g, 4.6 mmol, prepared according to Smaill, J. B., et al., Journal of Medicinal Chemistry, 2000, 43, 1380-1397). The reaction was quenched after stirring 30 min at 0° C. by a slow addition of saturated $NH_4Cl$, followed by extraction with EtOAc (100 mL). The organic layer was washed with $H_2O$ (2×50 mL), brine (50 mL), dried over $MgSO_4$, and concentrated to a yellow residue 2b, product was used directly for the next step. MS m/z (ESI+), 431 [M+1].

Steps 2, 3 and 4: preparation of (E)-N-(7-((3-oxabicyclo[3.1.0]hexan-6-ylmethoxy)-4-((3-chloro-4-fluorophenyl)amino)quinazolin-6-yl)-4-(dimethylamino)but-2-enamide (2)

The title compound (2) was prepared using the same procedures as in steps 2, 3 and 4 in Example 1, except that 2b was used in place of 1b. $^1$HNMR (CDCl$_3$, 300 MHz) δ 9.17 (s, 1H), 8.66 (s, 1H), 8.17 (s, 1H), 7.96 (m, 1H), 7.75 (s, 1H), 7.56 (m, 1H), 7.22 (s, 1H), 7.16 (m, 1H), 7.05 (m, 1H), 6.25 (d, 1H), 4.16 (d, 1H), 4.02 (d, 1H), 3.79 (d, 1H), 3.20 (d, 1H), 2.35 (s, 4H), 1.78 (s, 2H), 1.73 (s, 6H), 1.47 (m, 1H). MS (ESI) m/z=513 (MH$^+$).

The compound isolated after purification was predominantly the isomer of the structure (2-A), also referred to as "NT112".

Example 3

Preparation of (E)-N-(7-(((1S,5S)-3-oxabicyclo[3.1.0]hexan-1-yl)methoxy)-4-((3-chloro-4-fluorophenyl)amino)quinazolin-6-yl)-4-(dimethylamino)but-2-enamide (3)

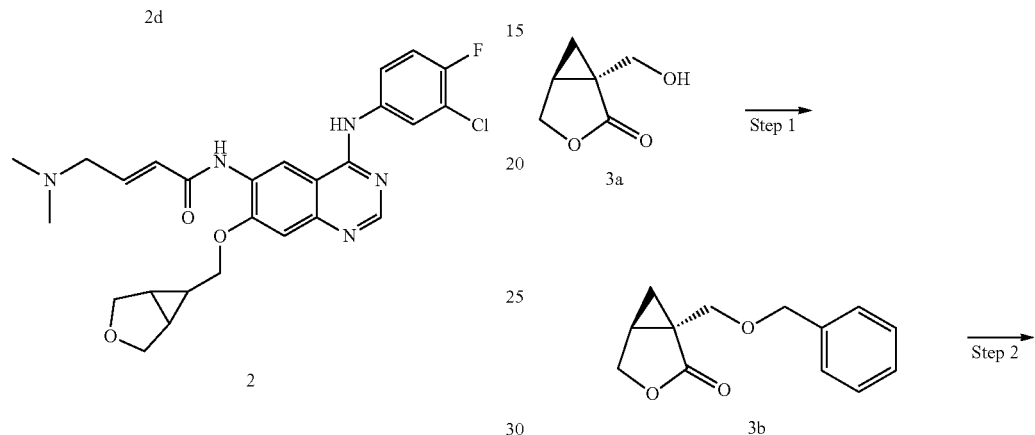

-continued

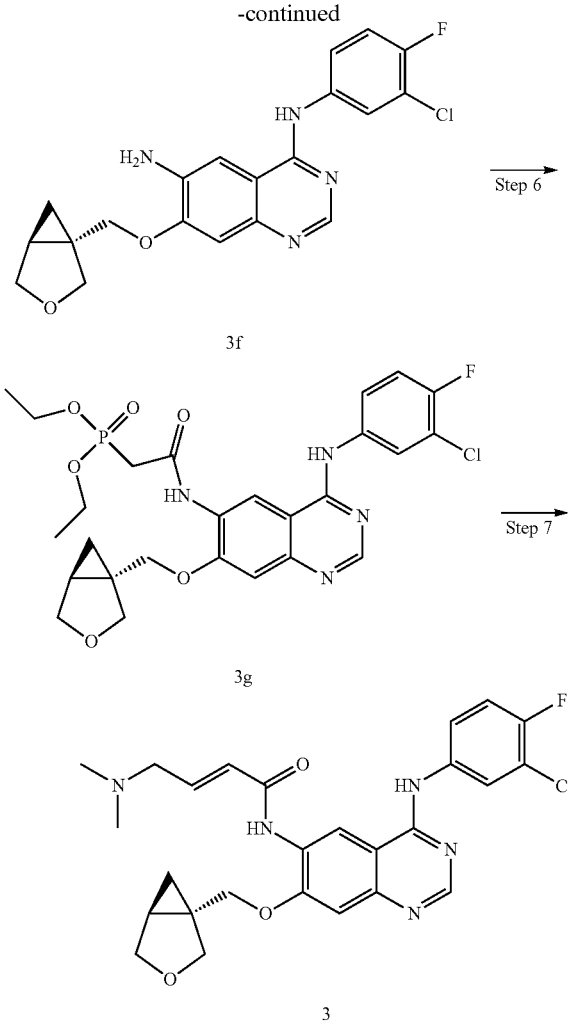

Step 1: preparation of (1R,5S)-1-((benzyloxy)methyl)-3-oxa-bicyclo[3.1.0]hexan-2-one (3b)

To a stirred solution of (1R,5S)-1-(hydroxymethyl)-3-oxa-bicyclo[3.1.0]hexan-2-one (3a, 100 mmol, prepared according to Moon, H. R., et al. Nucleosides, Nucleotides and Nucleic Acids, 2007, 26, 975-978) in THF (200 mL) at 0° C. was added NaH (60% in mineral oil, 4.80 g, 120 mmol). After 10 min, BnBr (120 mmol) was added. After stirring at room temperature for 12 h, the reaction was cooled to 0° C., and to the reaction was added saturate aqueous NH$_4$Cl (50 mL) and water (50 mL). The mixture was extracted with ether (300 mL). The organic layer was washed with water (100 mL), brine (50 mL), dried over MgSO$_4$, and concentrated. The residue was purified by column (0-20 ethyl acetate in hanexane) to give a colorless liquid (3b). LCMS (ESI) m/z=219 (M+1).

Step 2: Preparation of (1S,5S)-1-((benzyloxy)methyl)-3-oxa-bicyclo[3.1.0]hexane (3c)

The conditions in Sakai, N., et al. Synthesis, 2008 3533-3536 was used for this step. To a stirred mixture of (1R,5S)-1-((benzyloxy)methyl)-3-oxa-bicyclo[3.1.0]hexan-2-one (3b, 50 mmol) and InBr$_3$ (1.0 mmol) in chloroform (200 mL) was added triethylsilane (200 mmol). The mixture was then heated and stirred at 65° C. for 16 h, then cooled to room temperature. The reaction was concentrated. The residue was purified by column (0-10 ethyl acetate in hexane) to give a colorless liquid as pure (1S,5S)-1-((benzyloxy)methyl)-3-oxa-bicyclo[3.1.0]hexane (3c). MS (ESI) m/z=205 (M+1).

Step 3: Preparation of ((1R,5S)-3-oxa-bicyclo[3.1.0]hexan-1-yl)methanol (3d)

A mixture of (1S,5S)-1-((benzyloxy)methyl)-3-oxa-bicyclo[3.1.0]hexane (3c, 40 mmol) and Pd on carbon (wet, 5%) in MeOH (50 mL) was hydrogenated by a hydrogen balloon for 3 h. The mixture was then filtered through Celite™, and concentrated in vacuum to give the title compound ((1R,5S)-3-oxa-bicyclo[3.1.0]hexan-1-yl)methanol (3d), which was used for next step without purification.

Steps 4, 5, 6, and 7: preparation of (E)-N-(7-(((1S,5S)-3-oxa-bicyclo[3.1.0]hexan-1-yl)methoxy)-4-(3-chloro-4-fluorophenylamino)quinazolin-6-yl)-4-(dimethylamino)but-2-enamide (3)

The title compound (3) was prepared by exactly the same procedures as in steps 1, 2, 3 and 4 in example 2, except 3d was used in place of 2a. $^1$HNMR (CD$_3$OD, 300 MHz) δ 8.78 (s, 1H), 8.48 (s, 1H), 8.01 (m, 1H), 7.67 (m, 1H), 7.25 (m, 2H), 7.01 (m, 1H), 6.47 (d, 1H), 4.62 (s, 1H), 4.53 (d, 1H), 4.37 (d, 1H), 4.01 (d, 1H), 3.85 (m, 2H), 3.24 (d, 2H), 2.34 (s, 6H), 1.77 (m, 1H), 1.29 (s, 1H), 1.00 (m, 1H), 0.79 (m, 1H), 0.11 (s, 1H). MS (ESI) m/z=513 (MH$^+$).

Example 4

Preparation of (E)-N-(7-(((1R,5R)-3-oxabicyclo[3.1.0]hexan-1-yl)methoxy)-4-((3-chloro-4-fluorophenyl)amino)quinazolin-6-yl)-4-(dimethylamino)but-2-enamide (4)

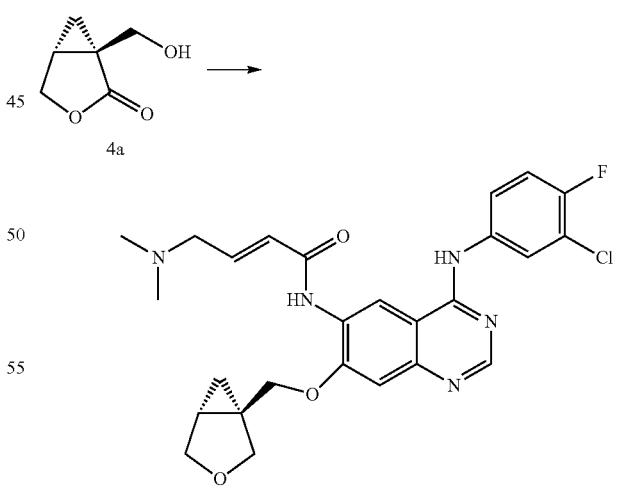

The title compound, (E)-N-(7-(((1R,5R)-3-oxa-bicyclo[3.1.0]hexan-1-yl)methoxy)-4-(3-chloro-4-fluorophenylamino)quinazolin-6-yl)-4-(dimethylamino)but-2-enamide (4) was prepared by the same procedures as in Example 3, except that 4a was used in place of 3a. $^1$HNMR (CD$_3$OD, 300

MHz) δ 8.73 (s, 1H), 8.44 (s, 1H), 8.00 (m, 1H), 7.67 (m, 1H), 7.20 (m, 2H), 7.01 (m, 1H), 6.50 (d, 1H), 4.52 (s, 1H), 4.53 (d, 1H), 4.38 (d, 1H), 4.01 (d, 1H), 3.85 (m, 3H), 3.24 (d, 2H), 2.34 (s, 6H), 1.77 (m, 1H), 0.9 (m, 1H), 0.81 (s, 1H), 0.78 (m, 1H). LCMS (ESI) m/z=512 (M+1).

Example 5

Preparation of (±)-(E)-N-(7-((3-oxa-bicyclo[3.1.0] hexan-1-yl)methoxy)-4-(3-chloro-4-fluorophenylamino)quinazolin-6-yl)-4-(dimethylamino)but-2-enamide (5)

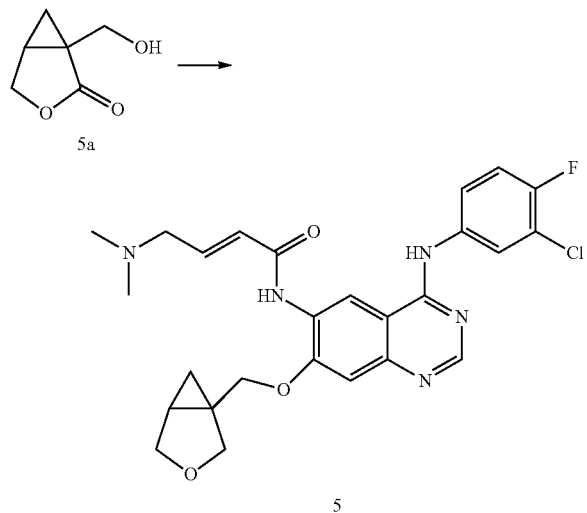

The title compound, (±)-(E)-N-(7-((3-oxa-bicyclo[3.1.0] hexan-1-yl)methoxy)-4-(3-chloro-4-fluorophenylamino)quinazolin-6-yl)-4-(dimethylamino)but-2-enamide (5) was prepared by the same procedures as in Example 3, except that 5a was used in place of 3a.

Example 6

Kinase Inhibition Assay

1) The compound is dissolved in DMSO to prepare a 10 mM solution, and was diluted to 100 micoM with water. When used for $IC_{50}$ measurement, series dilutions of 10 fold from 100 micoM are used. Kinase activity was determined with time-resolved Fret (TR-FRET) assay (LanthaScreen® kinase activity assay, from InVitrogen).

2) The assay is performed in a Black 384-well plate (from Corning). The kinase and the compound was incubated for 30 mM at room temperature. ATP (1 mM) and fluorescein-poly GT were added, and the reaction was incubated for 15 mM. Detection agent SA-XL665 (from Cisbio Assay) and TK Ab-Cryptate detection antibody (from InVitrogen) were added to stop the reaction.

3) The 384-well plate was sealed and incubated for 1 hour. The fluorescence was then measured at 620 nM (Cryptate) and 665 nM (XL655) wavelength.

4) Each concentration of compound was done in triplicate, and vehicle (without compound) and a positive control were used.

Data process: the ratio of fluorescence is calculated (value of fluorescence 665 nM over 620 nM). The results are calculated from: signal=compound fluorescence ratio–vehicle ratio, and the $IC_{50}$ was calculated based on inhibition curve.

The results, shown in Table 2, demonstrated that the EGFr and Her2 kinase inhibition $IC_{50}$ for compounds tested were below 100 nM.

Example 7

Cell Proliferation Inhibition Assay for BT474

1) Human breast cancer BT474 cells were plated 10000 cells/well in a 96-well clear tissue culture plate. The cells were incubated for 24 h at 37° C. to allow adherence.

2) A serials of concentrations of each compound (ranging from 30 uM to 0.16 nM, 5-fold dilution) in 96-well plate, and incubated for 72 h. Each concentration was tested in triplicate. During the cell proliferation assay, BT474 cells were cultured in the complete cell culture solution (low-glucose DMEM containing 5% FBS, 50 ug/ml gentamicin).

3) The culture medium was removed via aspiration, and the cell viability was detected by CCK-8 cell proliferation kit.

4) The $EC_{50}$ was calculated based on the proliferation curve.

The results in Table 2 show that BT474 cell growth inhibition $EC_{50}$ for compounds tested are below 100 nM.

TABLE 2

EGFR and ErbB2 (HER2) kinase inhibition, and BT474 cell proliferation inhibition assay results.

| Compound Example No. | EGFR Inhibition $IC_{50}$ (nM) | HER2 Inhibition $IC_{50}$ (nM) | BT474 Inhibition $IC_{50}$ (nM) |
|---|---|---|---|
| 1 | 0.4 | 25 | 35.9 |
| 2 | 0.13 | 6 | 19.1 |
| 3 | 0.54 | 23 | 31.8 |
| 4 | 0.51 | 22 | 25.6 |
| 5 | 0.37 | 91 | 157 |

Example 8

In Vivo Efficacy in NCI-H1975 Xenograft Mouse Model

H1975 cells were purchased from ATCC were cultured in RPMI1640+10% FBS+1% P/S antibiotics. Balb/c nude mice, female, 6-8 week, 18+2 g were purchased from Shanghai Laboratory Animal Co. Ltd. The purchased mice were adapted to the environment for 7 days before use, and were housed at 22-25° C. with humidity 40-70%, and light cycle with fluorescent light for 12-hour light (8:00-20:00) 12-hour dark.

Formulation: Erlotinib, afatinib (BIBW2992), and NT112 were dissolved in 2% DMA and 98% (40% HP-β-CD in deionized water).

The cancer cells (H1975) were amplified and implanted into the nude mice (right flank) with $5.0 \times 10^6$ cells in PBS and 1:1 with matrigel in a total volume of 0.1 ml/mouse. When the tumor reaches a volume of 200 (150-200) mm³, the tumor-bearing nude mice derived from H1975 cells were randomly assigned into several groups (10 mice/group), Group 1 served as vehicle; Groups 2 to 5 were administrated with afatinib at 20 mg/kg (p.o. q.d.), Compound NT112 at 10 mg/kg (po, qd); Compound NT112 at 20 mg/kg (po, qd) and erlotinib at 100 mg/kg (free base, p.o. q.d.); respectively. The animals were sacrificed after 4 weeks.

The mice were monitored twice daily for appearance and behavior, and for signs of morbidity and/or mortality. The tumor volume was measured twice a week, and the body weight was measured immediately before measuring the tumor volume throughout the whole study.

At end of the experiment (compound administration for four weeks), all the tumor-bearing mice were sacrificed by cervical dislocation under deep anesthesia. The tumor mass was resected, and weighed.

Tumor sizes were measured twice weekly in two dimensions using a caliper, and the volume was expressed in $mm^3$ using the formula: $V=½\times a\times b^2$ where a and b are the long and short diameters of the tumor, respectively. The tumor mass was weighed at the end of the experiment after harvested.

$V=½\times a\times b^2$ (a, b is maximum and minimum diameters respectively).

RTV(Relative Tumor Volume)=Vt/Vo

Vo is the tumor volume when the test article is initial administrated

Vt is the tumor volume of every measurement day after test article administration

T/C(%)=TRTV/CRTV×100%

TRTV: RTV of test article-treatment group; CRTV: RTV of control group Inhibition rate (%)=(average tumor volume of control group−average cancer volume of test article treatment group)/average tumor volume of control group×100%

Significant effective: T/C %<40%, P<0.05

Non-significant effective: T/C %>40%.

As shown in FIG. 1, Compound NT112 in this model is significantly more effective than erlotinib; and comparable with afatinib.

Example 9

In Vivo Efficacy in NCI-N87 Xenograft Mouse Model

NCI-N87 cell line was purchased from ATCC (American Type Culture Collection) and was cultured in RPMI1640+10% FBS+1% P/S antibiotics.

Male Balb/c nude mice, 6-8 week, 18±2 g (supplier: Shanghai SLAC Laboratory Animal Co. Ltd.) were used for the experiment. The purchased mice were adapted to the environment for 7 days before use, and were housed at 22-25° C. with humidity 40-70%, and light cycle with fluorescent light for 12-hour light (8:00-20:00) 12-hour dark. The mice have free access to food and water.

The cancer cells (NCI-N87) were implanted subcutaneous into the nude mice (right flank) with $5.0\times10^6$ cells in 0.1 ml PBS (50 mice). When the tumor size reaches a volume of 200 (150-200) $mm^3$, the tumor-bearing nude mice were randomly assigned into groups (10 mice/group), one group was served as vehicle, one group was administrated with Lapatinib ditosylate monoydrate (80 mg/kg, free base of Lapatinib, not salt, p.o. bid). The other two groups were administrated with NT112 (15 and 30 mg/kg, p.o. q.d, respectively). The administration period lasted for 4 weeks.

The mice were monitored twice daily for appearance and behavior, and for signs of morbidity and/or mortality. The tumor volume was measured twice a week, and the body weight was measured immediately before measuring the tumor volume throughout the whole study.

At end of the experiment (compound administration for four weeks), all the tumor-bearing mice were sacrificed by cervical dislocation under deep anesthesia. The tumor mass was resected, and weighed.

Tumor sizes were measured twice weekly in two dimensions using a caliper, and the volume was expressed in $mm^3$ using the formula: $V=½\times a\times b^2$ where a and b are the long and short diameters of the tumor, respectively. The tumor mass was weighed at the end of the experiment after harvested.

$V=½\times a\times b^2$ (a, b is maximum and minimum diameters respectively).

RTV(Relative Tumor Volume)=Vt/Vo

Vo is the tumor volume when the test article is initial administrated

Vt is the tumor volume of every measurement day after test article administration

T/C(%)=TRTV/CRTV×100%

TRTV: RTV of test article-treatment group; CRTV: RTV of control group Inhibition rate (%)=(average tumor volume of control group−average cancer volume of test article treatment group)/average tumor volume of control group×100%

The tumor-bearing mice were treated for 4 weeks with different doses of NT112 (15 mg/kg, 30 mg/kg, po, qd) and Lapatinib, 80 mg/kg, p.o., bid, 7 days/week. At the day-7 after treatment, the RTV T/C NT112 (15 mg/kg, 30 mg/kg) groups were <30%, and the tumor growth inhibition was >70%, but the RTV T/C was 31% and tumor growth inhibition rat was 69% in the lapatinib group. The same result was observed as well when it comes to the tumor weight. On day 28 after treatment, all the tumor-bearing mice were sacrificed, and all the tumor masses were harvested to weigh.

Lapatinib (GlaxoSmithKline), a small-molecule kinase inhibitor of EGFR and ErbB2, led to a tumor inhibition rate of 92.9% on day 28 (the last day of the study).

Figure 2:
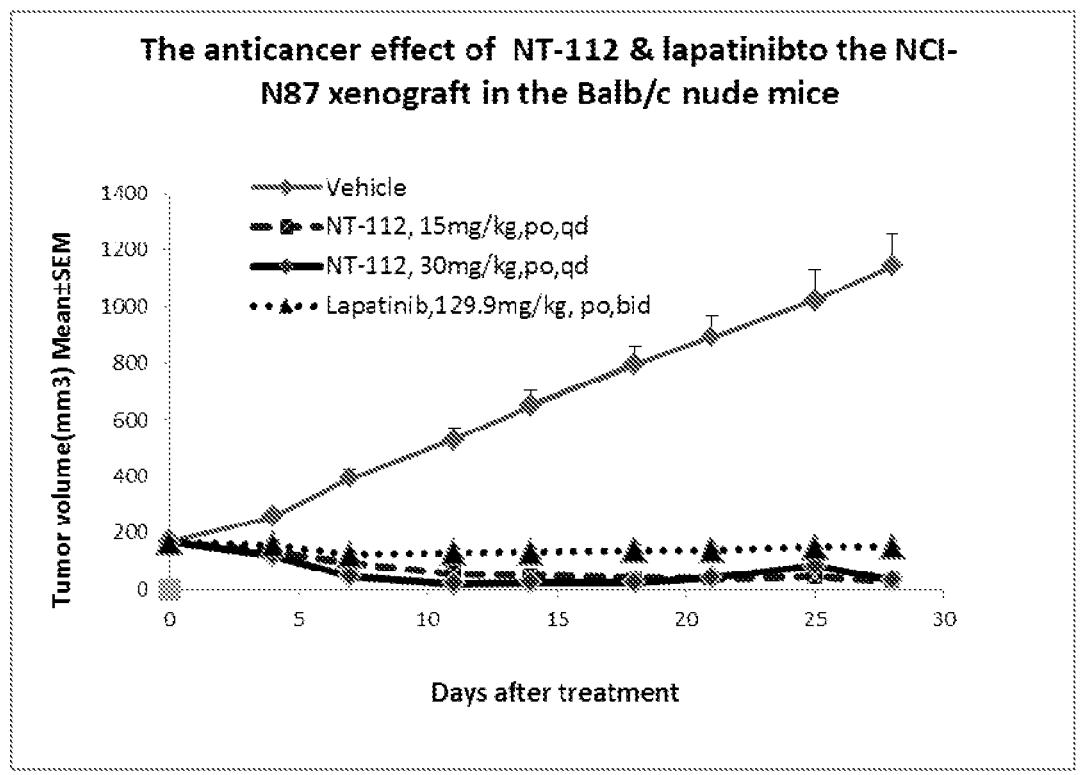
FIG. 2 shows the anticancer effect of Compound NT112 to the NCI-N87 xenograft in the Balb/c nude mice.

NT112 treatment with 30 mg/kg, p.o., qd, 7 days/week led to body weight loss in the NCI-N87 xenograft tumor model. The body weight started to decrease in NT112-treated on the day 3 after dosing in the 30 mg/kg, p.o., qd, 7 days/week, and continued to decrease until reached the maximal body weight loss on day 11. The administration of the high dose (30 mg/kg) NT112 was stopped and never resumed. The body weight recovered to normal by day 28. The 15 mg/kg, po, qd dosing group was continued without predefined side effect. See FIG. 2.

As used herein, the term "po", "p.o." or "PO", used in combination with the term "qd" or "q.d.", means oral administration, once a day.

Example 10

Pharmacokinetics Studies in Mice

Sample Preparation:

The test article each was dissolved in 10% DMSO and 90% of (40% HP-β-CD in deionized water) to yield concentration at 0.4 mg/mL for intravenous administration, and 1 mg/mL for oral administration.

Method development and plasma samples analysis were performed by Analytical Sciences Division of the Testing Facility by means of LC-MS/MS. The analytical results were confirmed using quality control samples for intra-assay variation (within day variation). The accuracy of >66% of the quality control samples was between 80-120% of the known value(s).

Each group is consisted 30 CD-1 mice (supplied by Sino-British SIPPR/BK Lab. Animal Ltd., Co, Shanghai), 5-8 week old, 20-28 g body weight. The test articles were administered by a single bolus intravenous injection or via oral gavage.

All animals were observed for morbidity, mortality, injury, and availability of food and water twice per day during the acclimation and study periods. Any animals in poor health were identified for further monitoring or possible euthanasia.

Blood samples (at least 300 µL/sample) were collected via cardiac puncture after euthanasia by carbon dioxide inhalation at appropriate time points for determination of the plasma concentrations of the test article. Samples were placed in tubes containing $K_3$-EDTA and stored on ice until centrifuged.

Three mice in each group were used for blood collection at each of the 10 time points (Groups 1-10): Pre-dose and post-dose at 5 min, 15 min, 30 min, 1 h, 2 h, 4 h, 6 h, 8 h and 24 h.

Analysis:

The PK blood samples were centrifuged at approximately 8000 rpm for 6 minutes at 2-8° C. and the resulting plasma were separated and stored frozen at approximately −80° C. (following separation, the plasma may be initially placed on ice prior to being stored in the −80° C. freezer). All the plasma samples were labeled with detailed information such as study number, animal number, matrix, time points of collection and date of collection.

Standard set of parameters including Area Under the Curve ($AUC_{(0-t)}$ and $AUC_{(0-\infty)}$), elimination half-live ($T_{1/2}$), maximum plasma concentration ($C_{max}$), time to reach maximum plasma concentration ($T_{max}$), clearance (CL), and volume of distribution ($V_z$) were calculated using noncompartmental analysis modules in FDA certified pharmacokinetic program WinNonlin Professional v5.2 (Pharsight, USA) by the Study Director. Furthermore, the Bioavailability was estimated using the following formula:

$$F = \frac{AUC_{(0-\infty)(PO)} \times Dose_{IV}}{AUC_{(0-\infty)(IV)} \times Dose_{(PO)}} \times 100\%$$

Figure 3:
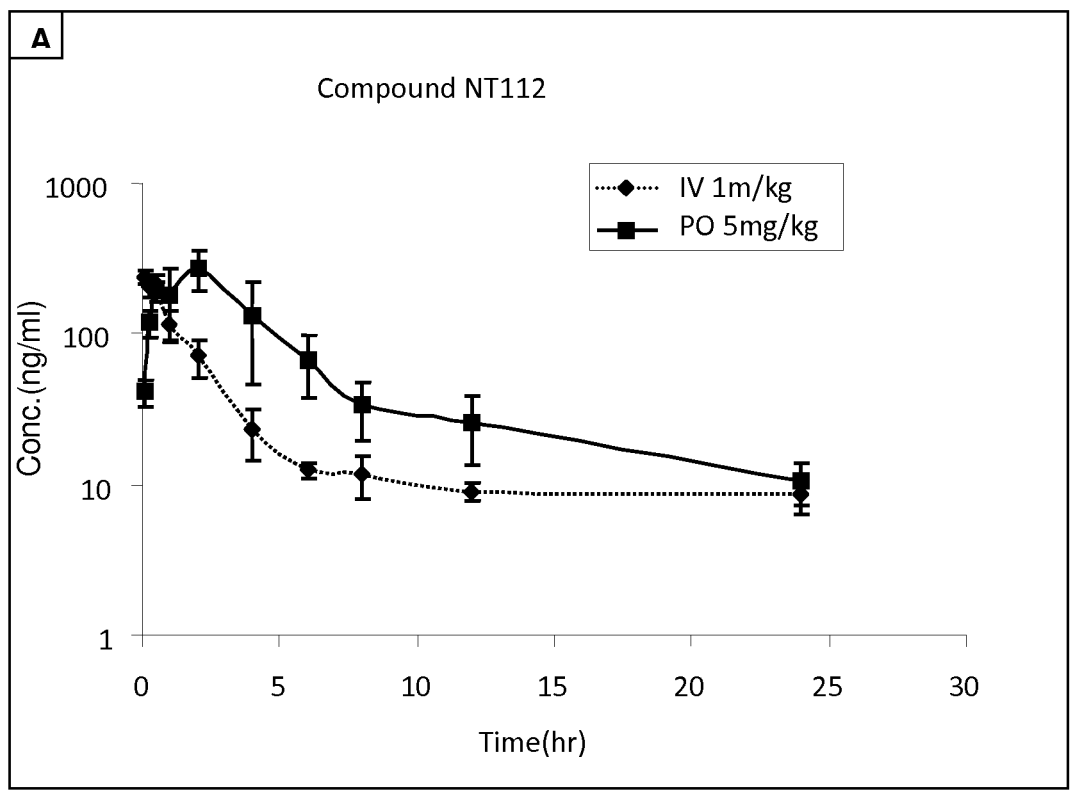
FIGS. 3-A and B show the mouse pharmacokinetics data for Compound NT112 and afatinib respectively.
Figure 3:
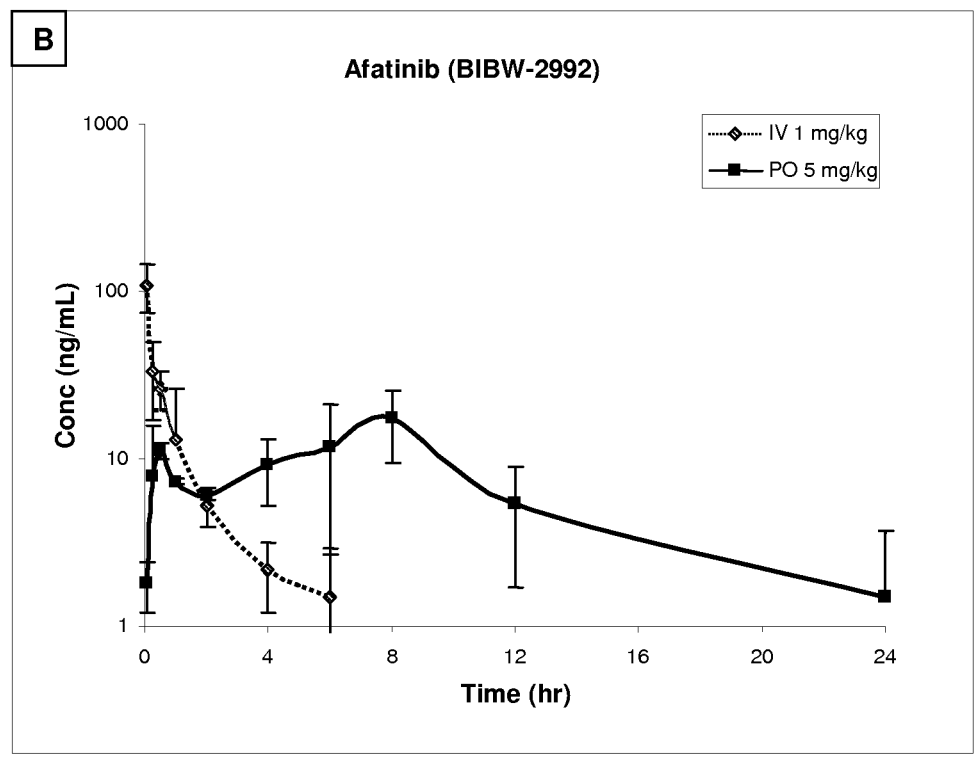

ABBREVIATIONS $AUC_{(0-t)}$ Area under the curve from the time of dosing to the last measurable concentration $AUC_{(0-\infty)}$ Area under the curve from the time of dosing extrapolated to infinity, based on the last observed concentration CL Total body clearance, CL=Dose/AUC $C_{max}$ Maximum observed concentration, occurring at $T_{max}$ F Bioavailability $MRT_{(0-\infty)}$ Mean residence time from the time of dosing to infinity $T_{max}$ Time of maximum observed concentration $T_{1/2}$ Terminal half-life=ln(2)λz $V_z$ Volume of distribution based on the terminal phase Mouse pharmacokinetics (PK) of NT112 (Compound 2-A) and afatinib (BIBW-2992) are shown in FIG. 3, Panels A and B respectively; and the rat PK parameters are listed in Tables 3 and 4 respectively.

TABLE 3

Mouse PK parameters measured for Compound NT112

| Plasma PK Parameters | $C_{max}$ ng/mL | $T_{1/2}$ hr | CL L/h/Kg | $V_z$ L/Kg | $AUC_{0-t}$ ng*hr/mL | $AUC_{0-\infty}$ ng*hr/mL | F % |
|---|---|---|---|---|---|---|---|
| IV 1 mg/Kg | 236 | 4.44 | 1.69 | 3.26 | 575 | 592 | 100 |
| PO 5 mg/Kg | 272 | 11.1 | 3.40 | 16.4 | 1420 | 1471 | 49.7 |

TABLE 4

Mouse PK parameters measured for afatinib (BIBW-2992)

| Plasma PK Parameters | $C_{max}$ ng/mL | MRT hr | CL L/h/Kg | $V_z$ L/Kg | $AUC_{0-t}$ ng*hr/mL | F % |
|---|---|---|---|---|---|---|
| IV 1 mg/Kg | 109 | 1.6 | 0.52 | 1.3 | 54 | 100 |
| PO 5 mg/Kg | 17.6 | 9.3 | 0.84 | 6.3 | 167 | 62.0 |

Based on the PK data generated from mouse and rat, it is likely that NT112 will have superior pharmacokinetic properties in human and other mammals, therefore possibly exhibit superior anticancer activities.

Example 11

Pharmacokinetics Studies in Rats

Sample Preparation:

The test article each was dissolved in 10% DMSO and 90% of (40% HP-β-CD in deionized water) to yield concentration at 0.4 mg/mL for intravenous administration, and 1 mg/mL for oral administration.

Method development and plasma samples analysis were performed by Analytical Sciences Division of the Testing Facility by means of LC-MS/MS. The analytical results were confirmed using quality control samples for intra-assay variation (within day variation). The accuracy of >66% of the quality control samples was between 80-120% of the known value(s).

Each group consisted 3 male Sprauge Dawley rats (7-8 week old, 200-300 g body weight). The test articles were administered by a single bolus intravenous injection via the lateral tail vein or via oral gavage.

Blood samples (approximately 300 µl) were collected via retro-orbital puncture after anaesthesia using mixed gas ($CO_2:O_2=7:3$) into tubes containing EDTA-K3 anticoagulant at appropriate time points. 10 time points (Groups 1-2): Pre-dose and post-dose at 5 min, 15 min, 30 min, 1 h, 2 h, 4 h, 6 h, 8 h and 24 h.

Analysis:

The PK blood samples were processed and analyzed using the same methods as in Example 10.

Figure 4:
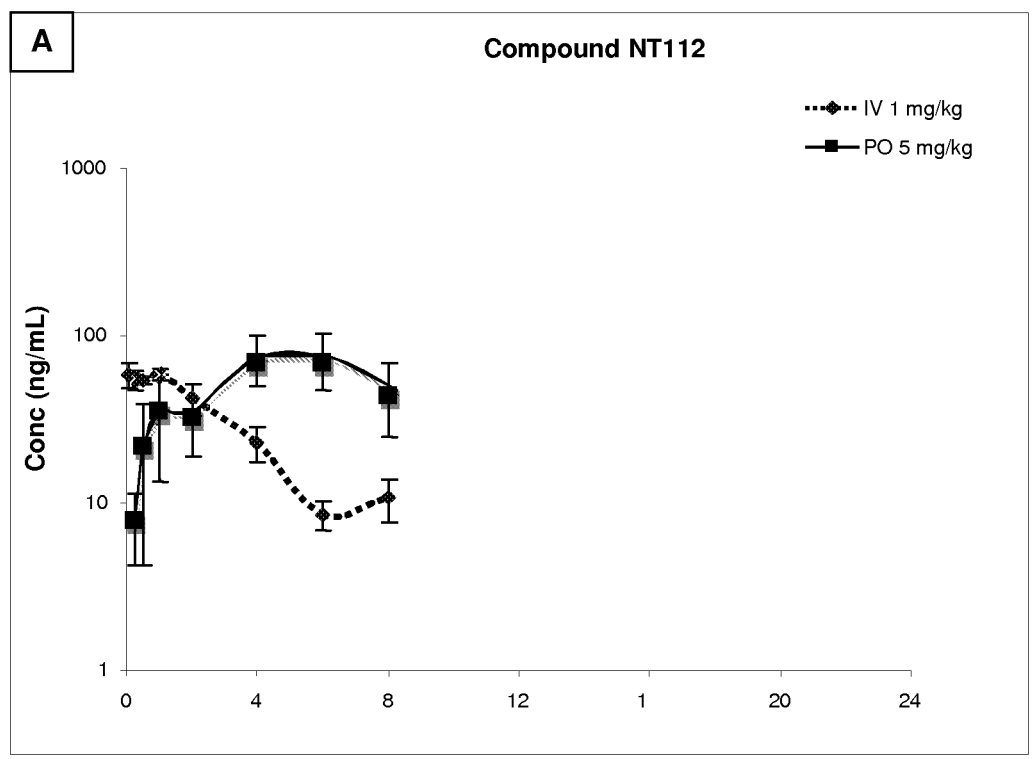
FIGS. 4-A and B show the rat pharmacokinetics data for Compound NT112 and afatinib respectively. The structure of afatinib (also known as BIBW-2992) is also shown in FIG. 4-B.
Figure 4:
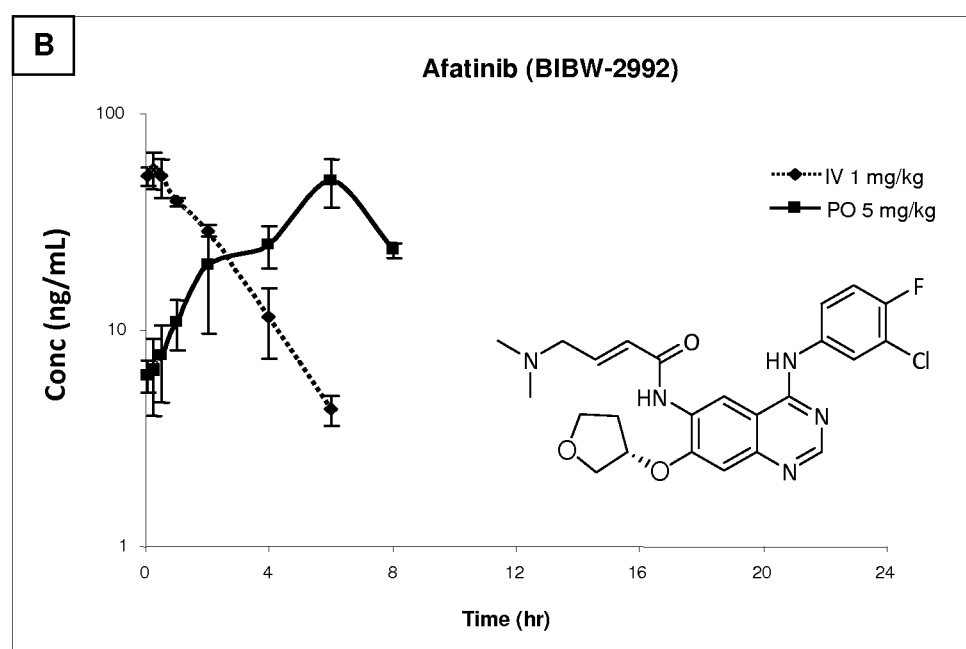

Rat pharmacokinetics (PK) of NT112 (Compound 2-A) and afatinib (BIBW-2992) are shown in FIG. 4, Panels A and B respectively; and the rat PK parameters are listed in Tables 5 and 6 respectively.

TABLE 5

Rat PK parameters measured for Compound NT112

| Plasma PK Parameters | $C_{max}$ ng/mL | $T_{1/2}$ hr | CL L/h/Kg | $V_z$ L/Kg | $AUC_{0-t}$ ng*hr/mL | $AUC_{0-\infty}$ ng*hr/mL | F % |
|---|---|---|---|---|---|---|---|
| IV 1 mg/Kg | 59.3 | 6.05 | 4.03 | 10.58 | 220 | 248 | 100 |
| PO 5 mg/Kg | 74.9 | 20.03 | 5.93 | 51.55 | 434 | 843 | 68.0 |

Note:
estimate of oral bioavailability may contain large uncertainty due to the flat nature of the PO data at the last three observable data points. As a comparison, if using AUC(0-t) instead of AUC(0-∞), the calculated oral bioavailability becomes 39.5%.

TABLE 6

Rat PK parameters measured for afatinib (BIBW-2992)

| Plasma PK Parameters | $C_{max}$ ng/mL | $T_{1/2}$ hr | CL L/h/Kg | $V_z$ L/Kg | $AUC_{0-t}$ ng*hr/mL | $AUC_{0-\infty}$ ng*hr/mL | F % |
|---|---|---|---|---|---|---|---|
| IV 1 mg/Kg | 55.6 | 5.12 | 6.82 | 15.17 | 137 | 147 | 100 |
| PO 5 mg/Kg | 49.2 | 11.02 | 15.26 | 73.02 | 215 | 328 | 44.7 |

Note:
estimate of oral bioavailability may contain large uncertainty due to the flat nature of the PO data at the last three observable data points. As a comparison, if using AUC(0-t) instead of AUC(0-∞), the calculated oral bioavailability becomes 31.4%.

Compound NT112 showed higher exposure and better oral bioavailability with oral administration, compared to afatinib (bibw-2992), a structurally similar compound.

As used herein and in the appended claims, the singular forms "a," "an," and "the" include plural reference unless the context clearly indicates otherwise.

It is understood that aspect and variations of the invention described herein include "consisting" and/or "consisting essentially of" aspects and variations.

FURTHER EMBODIMENTS OF THE INVENTION

Embodiment 1

A compound of Formula (I):

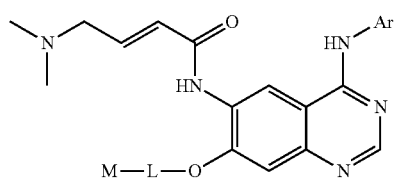

Formula (I)

or a stereoisomer, geometric isomer, tautomer, hydrate, solvate, polymorph, metabolite, pharmaceutically acceptable salt or prodrug, thereof, wherein:

Ar is a substituted monocyclic phenyl or monocyclic heteroaryl, optionally substituted with 0-4 groups selected from halogen, trifluoromethyl, trifluomethoxy, $C_{1-3}$ alkyl, ethynyl, ethenyl, $C_{1-3}$ alkoxyl; or $O(CH_2)_n Ar^1$, wherein n is 0 or 1;

$Ar^1$ is selected form monocyclic aryl or 5-6 membered heteroaryl group, and the aryl or heteroaryl may be substituted with 0-3 groups selected from halogen, trifluoromethyl, trifluomethoxy, $C_{1-3}$ alkyl, $C_{2-3}$ alkynyl, $C_{2-3}$ alkenyl, and $C_{1-3}$ alkoxyl;

L is a bond or $CH_2$;

M is a 6-10 membered bicyclic heterocycle, containing one or more O, N, or S atoms, and the heterocycle may be further substituted with one or more halogen, $C_{1-3}$ alkyl, hydroxyl, or $C_{1-3}$ alkoxyl.

Embodiment 2

The compound of embodiment 1, wherein Ar is selected from the following structures:

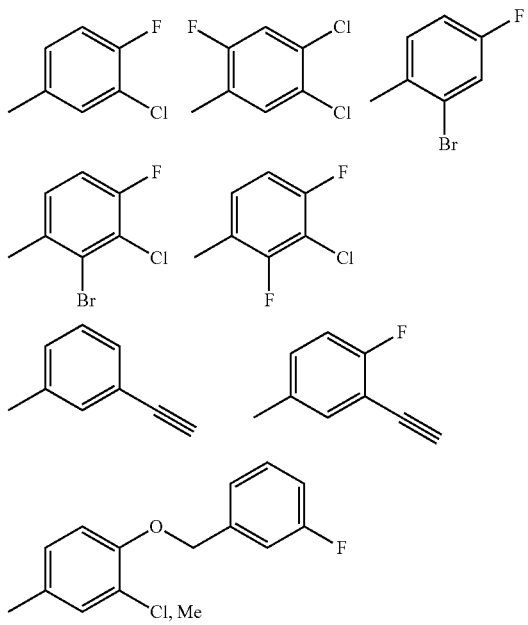

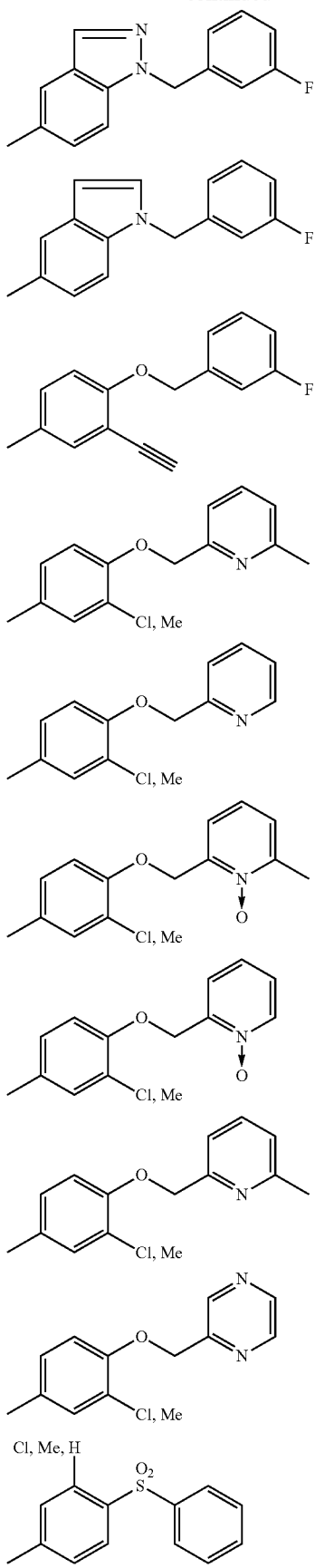
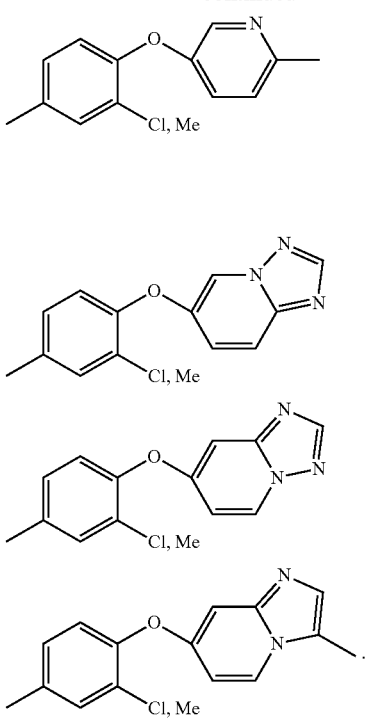
Embodiment 3
The compound of embodiment 1, wherein the compound is selected from:
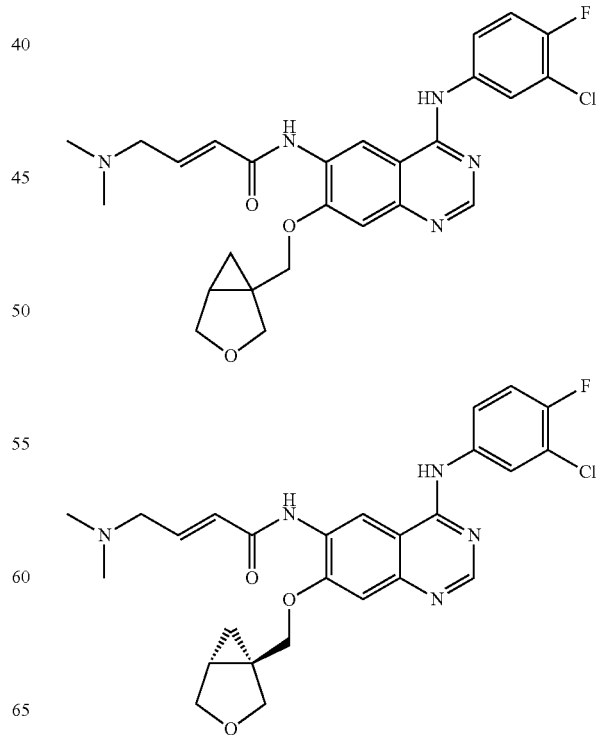

47
-continued

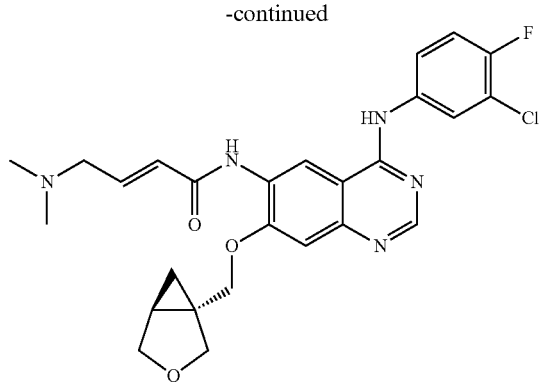

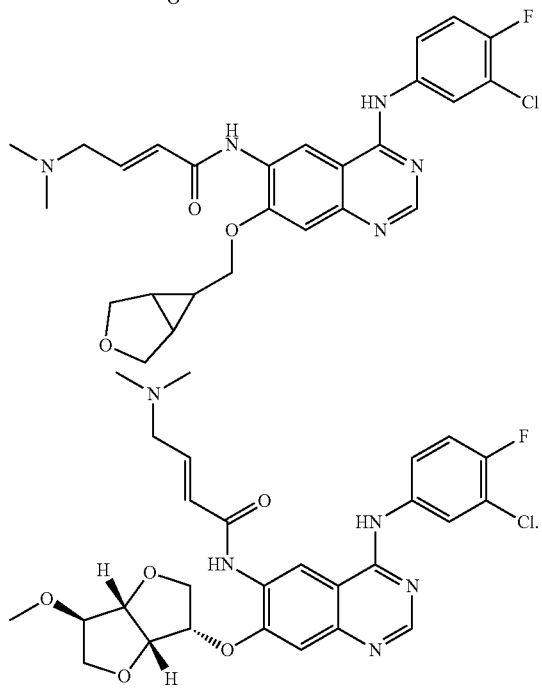

Embodiment 4

The compound of embodiment 1, wherein the pharmaceutically acceptable salt thereof is a salt is formed with an acid selected from: malic acid, lactic acid, maleic acid, fumaric acid, succinic acid, hydrochloric acid, methanesulfonic acid, toluenesulfonic acid, benzenesulfonic acid, sulfuric acid, phosphoric acid, citric acid, tartaric acid, acetic acid, propionic acid, caprylic, caproic acid, and benzoic acid.

Embodiment 5

A pharmaceutical composition comprising a compound of embodiment 1, or a stereoisomer, geometric isomer, tautomer, hydrate, solvate, polymorph, metabolite, pharmaceutically acceptable salt or prodrug, and a pharmaceutically acceptable carrier, excipient, diluent, adjuvant, vehicle, or a combination thereof.

Embodiment 6

Use of a compound of any one of embodiments 1-4 or a pharmaceutical composition of embodiment 5 in the manufacture of a medicament for the treatment of a receptor protein tyrosine kinase-related disease or an inhibitor of receptor protein tyrosine kinase.

Embodiment 7

The use according to embodiment 6, wherein the receptor protein tyrosine kinase-related disease, includes but not limited to: breast cancer, colorectal cancer, lung cancer, papillary carcinoma, prostate cancer, lymphoma, colonpancreatic cancer, ovarian cancer, cervical cancer, central nervous system cancer, osteogenic sarcoma, kidney cancer, liver cancer, bladder cancer, gastric cancer, head and neck squamous cell carcinoma, melanoma and leukemia.

Embodiment 8

A method for the treatment of a receptor protein tyrosine kinase-related disease comprising administering to a subject in need thereof an effective dose of a compound of embodiment 1 or a pharmaceutical composition of embodiment 5.

Embodiment 9

A method for making a compound of embodiment 1, comprising the steps of:

Step 1: reacting compound Ia with aniline to obtain compounds Ib;

Step 2: treating alcohol M-L-OH with strong base, and then adding compound Ib to obtain compound Ic;

Step 3: reducing compound Ic to produce compounds Id;

Step 4: coupling Id with acid Ie using a coupling reagent to form amide If;

Step 5: producing a compound of formula (I) by a Wittig reaction of compound If with 2-dimethylaminoacetaldehyde.

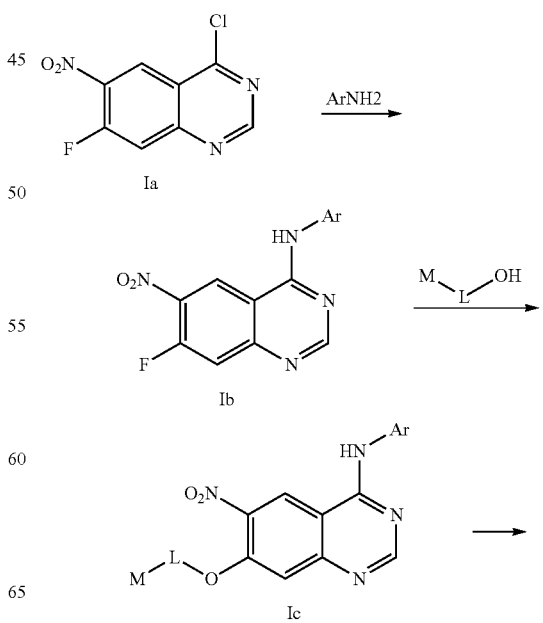

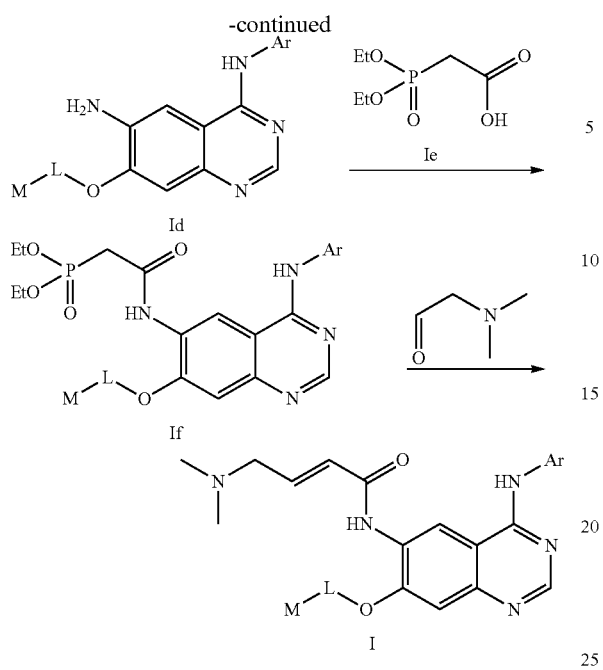

wherein:

Ar is a substituted monocyclic phenyl or monocyclic heteroaryl, optionally substituted with 0-4 groups selected from halogen, trifluoromethyl, trifluomethoxy, $C_{1-3}$ alkyl, ethynyl, ethenyl, $C_{1-3}$ alkoxyl; or $O(CH_2)_n Ar^1$, wherein n is 0 or 1;

$Ar^1$ is selected form monocyclic aryl or 5-6 membered heteroaryl group, and the aryl or heteroaryl may be substituted with 0-3 groups selected from halogen, trifluoromethyl, trifluomethoxy, $C_{1-3}$ alkyl, $C_{2-3}$ alkynyl, $C_{2-3}$ alkenyl, and $C_{1-3}$ alkoxyl;

L is a bond or $CH_2$;

M is a 6-10 membered bicyclic heterocycle, containing one or more O, N, or S atoms, and the heterocycle may be further substituted with one or more halogen, $C_{1-3}$ alkyl, hydroxyl, or $C_{1-3}$ alkoxyl.

Embodiment 10

The method of embodiment 9, wherein the strong base in step 2 is sodium hydride.

Embodiment 11

The method of embodiment 9, wherein the reducing in step 3 is Pt-C catalyzed hydrogenation, iron powder-acid catalyzed.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

The disclosures of all patent and scientific literature cited herein are expressly incorporated in their entirety by reference.

What is claimed is:

1. A compound of the formula (I):

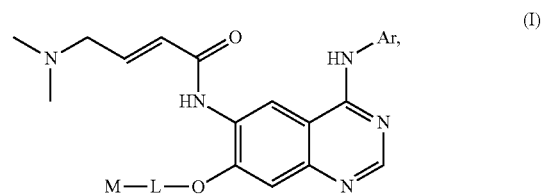

or a salt thereof, wherein:

Ar is a monocyclic aryl or monocyclic heteroaryl, optionally substituted with 0 to 4 substituents independently selected from the group consisting of halogen, trifluoromethyl, trifluoromethoxy, $C_1$-$C_3$ alkyl, ethynyl, ethenyl, $C_1$-$C_3$ alkoxy, —O(CH$_2$)$_n$Ar$^1$; —(CH$_2$)$_m$Ar$^2$ and —S(O)$_2$Ar$^3$;

or Ar is selected from the group consisting of:

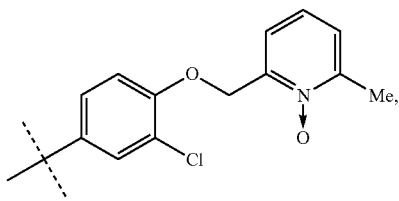

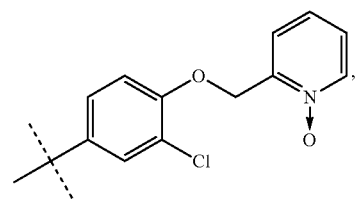

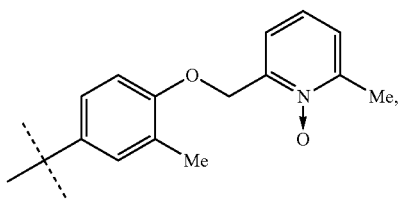

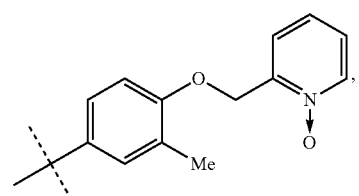

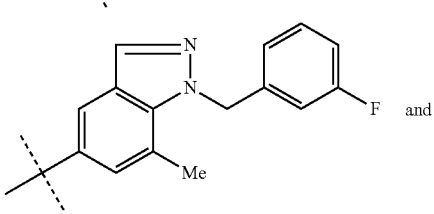

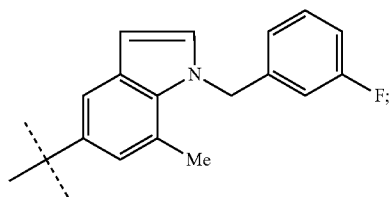

m and n are independently 0 or 1;

each Ar$^1$, Ar$^2$ and Ar$^3$ is independently a monocyclic aryl or 5 or 6 membered heteroaryl, where each aryl or heteroaryl is optionally substituted with 0 to 3 substituents independently selected from the group consisting of halogen, trifluoromethyl, trifluoromethoxy, $C_1$-$C_3$ alkyl, $C_2$-$C_3$ alkynyl, $C_2$-$C_3$ alkenyl and $C_1$-$C_3$ alkoxy;

L is a bond or CH$_2$; and

M is a 6-10 membered bicyclic heterocycle containing one or more annular heteroatoms independently selected from O and S, optionally substituted with one or more substituents independently selected from the group consisting of halogen, $C_1$-$C_3$ alkyl, hydroxyl and $C_1$-$C_3$ alkoxy.

2. The compound of claim 1, or a salt thereof, wherein Ar is a phenyl optionally substituted with 0 to 4 substituents independently selected from the group consisting of halogen, trifluoromethyl, trifluoromethoxy, $C_1$-$C_3$ alkyl, ethynyl, ethenyl, $C_1$-$C_3$ alkoxy, —O(CH$_2$)$_n$Ar$^1$; —(CH$_2$)$_m$Ar$^2$ and —S(O)$_2$Ar$^3$.

3. The compound of claim 2, or a salt thereof, wherein Ar is a phenyl substituted with 1 to 3 substituents independently selected from the group consisting of halogen, trifluoromethyl, trifluoromethoxy, $C_1$-$C_3$ alkyl, ethynyl, ethenyl, $C_1$-$C_3$ alkoxy, —O(CH$_2$)$_n$Ar$^1$; —(CH$_2$)$_m$Ar$^2$ and —S(O)$_2$Ar$^3$.

4. The compound of claim 1, or a salt thereof, wherein Ar is selected from the group consisting of:

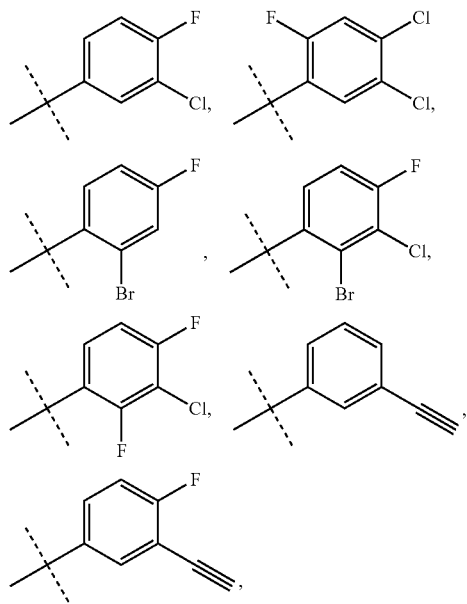

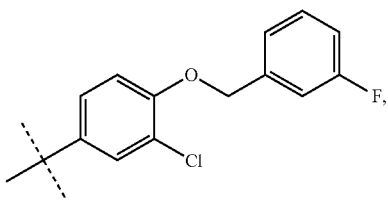

-continued

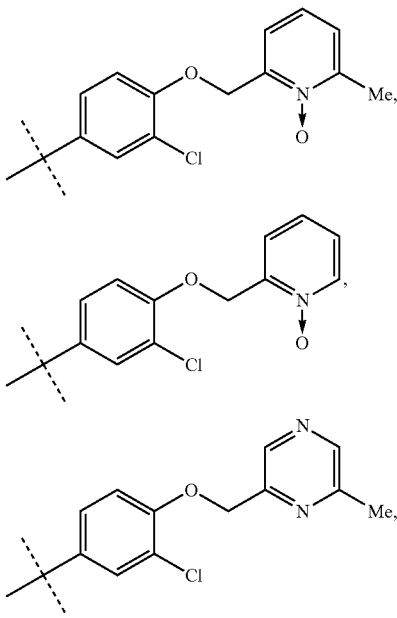

-continued
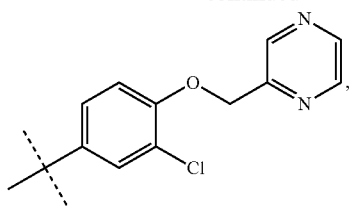
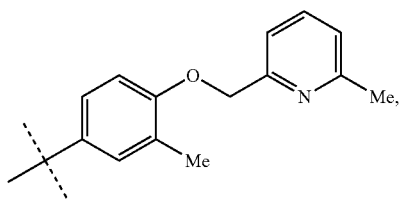
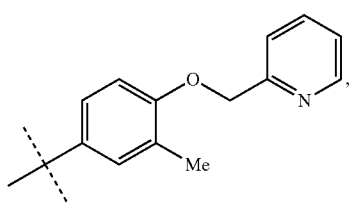
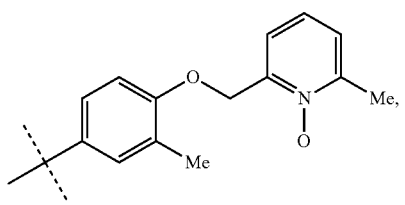
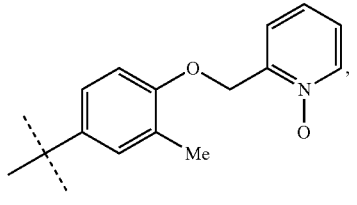
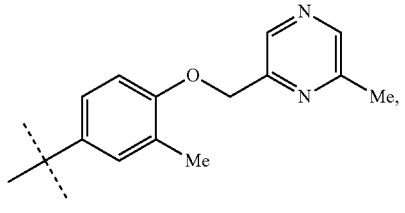
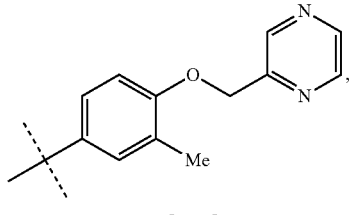
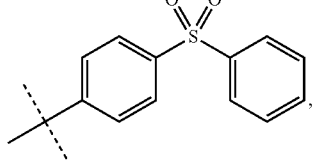
-continued
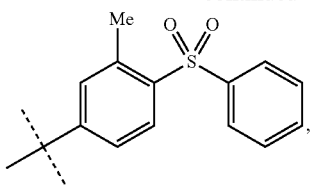
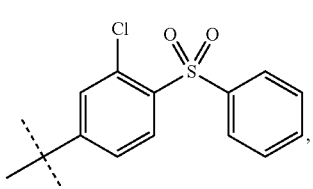
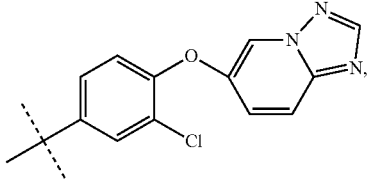
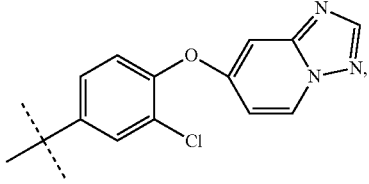
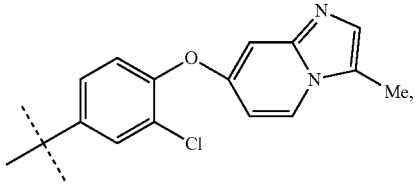
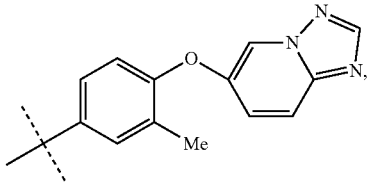
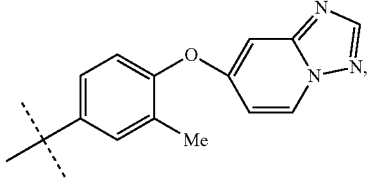
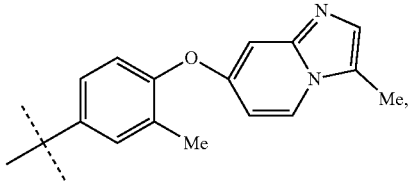
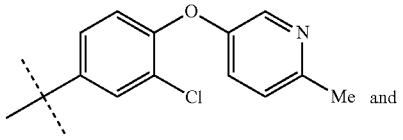
and -continued

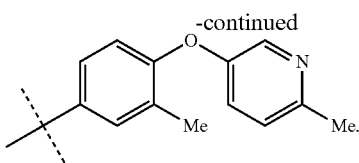

5. The compound of claim 3, or a salt thereof, wherein Ar is 3-chloro-4-fluorophenyl.

6. The compound of claim 1, or a salt thereof, wherein Ar is a monocyclic heteroaryl optionally substituted with 0 to 4 substituents independently selected from the group consisting of halogen, trifluoromethyl, trifluoromethoxy, $C_1$-$C_3$ alkyl, ethynyl, ethenyl, $C_1$-$C_3$ alkoxy, —O(CH$_2$)$_n$Ar$^1$; —(CH$_2$)$_m$Ar$^2$ and —S(O)$_2$Ar$^3$.

7. The compound of claim 1, or a salt thereof, wherein Ar is selected from the group consisting of:

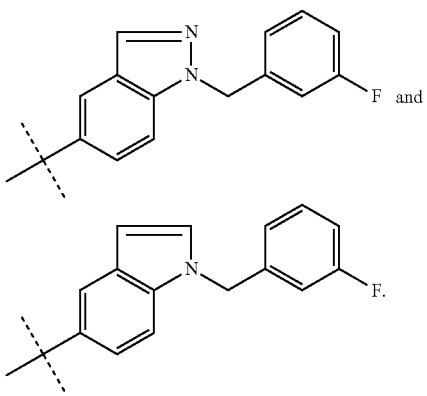

8. The compound of claim 1, or a salt thereof, wherein L is a bond.

9. The compound of claim 1, or a salt thereof, wherein L is a CH$_2$.

10. The compound of claim 1, or a salt thereof, wherein M is a 6-10 membered bicyclic heterocycle containing one or more annular heteroatoms selected from O, substituted with one or more substituents selected from the group consisting of halogen, $C_1$-$C_3$ alkyl, hydroxyl and $C_1$-$C_3$ alkoxy.

11. The compound of claim 10, or a salt thereof, wherein M is

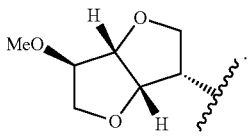 [SMILES: *[C@H]1CO[C@@H]2[C@H]1OC[C@H]2OC ; "."]

12. The compound of claim 1, or a salt thereof, wherein M is an unsubstituted 6-10 membered bicyclic heterocycle containing one or more annular heteroatoms selected from O.

13. The compound of claim 1, or a salt thereof, wherein M is a 6-10 membered bicyclic heterocycle containing one annular heteroatom selected from O and S.

14. The compound of claim 13, or a salt thereof, wherein the one annular heteroatom is oxygen.

15. The compound of claim 14, or a salt thereof, wherein M is 3-oxabicyclo[3.1.0]hexan-6-yl or 3-oxabicyclo[3.1.0]hexan-1-yl.

16. The compound of claim 13, or a salt thereof, wherein M is 3-oxabicyclo[3.1.0]hexan-6-yl.

17. The compound of claim 1, wherein the compound is selected from the group consisting of:
- (E)-N-(7-((3R,3aS,6S,6aS)-hexahydro-3-methoxyfuro[3,2-b]furan-6-yloxy)-4-(3-chloro-4-fluorophenylamino)quinazolin-6-yl)-4-(dimethylamino)but-2-enamide,
- (E)-N-(7-((3-oxa-bicyclo[3.1.0]hexan-6-yl)methoxy)-4-(3-chloro-4-fluorophenylamino)quinazolin-6-yl)-4-(dimethylamino)but-2-enamide,
- (E)-N-(7-(((1R,5S,6r)-3-oxa-bicyclo[3.1.0]hexan-6-yl)methoxy)-4-(3-chloro-4-fluorophenylamino)quinazolin-6-yl)-4-(dimethylamino)but-2-enamide,
- (E)-N-(7-(((1R,5S,6s)3-oxa-bicyclo[3.1.0]hexan-6-yl)methoxy)-4-(3-chloro-4-fluorophenylamino)quinazolin-6-yl)-4-(dimethylamino)but-2-enamide,
- (E)-N-(7-(((1S,5S)-3-oxa-bicyclo[3.1.0]hexan-1-yl)methoxy)-4-(3-chloro-4-fluorophenylamino)quinazolin-6-yl)-4-(dimethylamino)but-2-enamide,
- (E)-N-(7-(((1R,5R)-3-oxa-bicyclo[3.1.0]hexan-1-yl)methoxy)-4-(3-chloro-4-fluorophenylamino)quinazolin-6-yl)-4-(dimethylamino)but-2-enamide, and
- (E)-N-(7-((3-oxa-bicyclo[3.1.0]hexan-1-yl)methoxy)-4-(3-chloro-4-fluorophenylamino)quinazolin-6-yl)-4-(dimethylamino)but-2-enamide;

or a salt thereof.

18. The compound of claim 1, wherein the compound is of the formula:

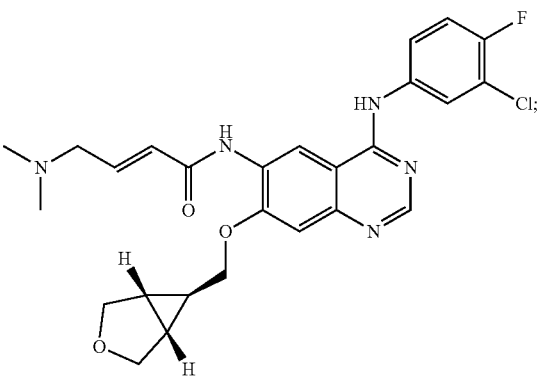 [SMILES: CN(C)C/C=C/C(=O)Nc1cc2c(Nc3ccc(F)c(Cl)c3)ncnc2cc1OC[C@H]1[C@@H]2COC[C@@H]21]

or a salt thereof.

19. A pharmaceutical composition comprising a compound of claim 1, or a salt thereof; and a pharmaceutically acceptable carrier.

20. A kit comprising a compound of claim 1, or a salt, solvate, of physiologically functional derivative thereof.

21. A method for treating a receptor protein tyrosine kinase-related disease in an individual in need thereof comprising administering to the individual an effective amount of a compound of claim 1, or a salt, solvate, polymorph, metabolite or prodrug thereof, wherein the receptor protein tyrosine kinase-related disease is a lung cancer or a gastric cancer.

22. The method of claim 21, wherein the receptor protein tyrosine kinase-related disease is a lung cancer.

23. The method of claim 21, wherein the receptor protein tyrosine kinase-related disease is a gastric cancer.

24. The method of claim 22, wherein the lung cancer is a non-small cell lung cancer.

25. A method for treating a receptor protein tyrosine kinase-related disease in an individual in need thereof comprising administering to the individual an effective amount of a compound of claim 18, or a salt thereof, wherein the receptor protein tyrosine kinase-related disease is a lung cancer or a gastric cancer.

26. The method of claim 25, wherein the receptor protein tyrosine kinase-related disease is a lung cancer.

27. The method of claim 25, wherein the receptor protein tyrosine kinase-related disease is a gastric cancer.

28. The method of claim 26, wherein the lung cancer is a non-small cell lung cancer.

29. A method for making a compound of claim 1, comprising the steps of:

Step 1: reacting compound of formula (Ia):

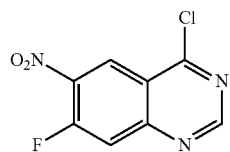

with a compound of formula ArNH$_2$ to obtain a compound of the formula (Ib):

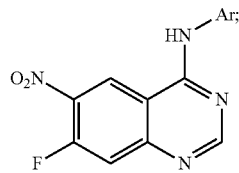

Step 2: treating an alcohol of the formula M-L-OH with a strong base, and then adding the compound of the formula (Ib) to obtain a compound of the formula (Ic):

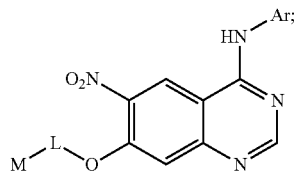

Step 3: reducing the compound of the formula (Ic) to produce a compound of the formula (Id):

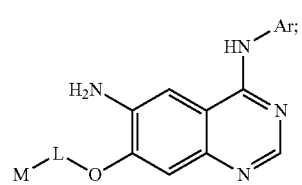

Step 4: coupling the compound of the formula (Id) with an acid of the formula (Ie):

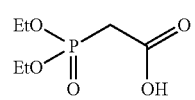

using a coupling reagent to form an amide of the formula (If):

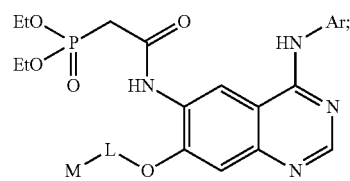

and

Step 5: producing a compound of the formula (I) by a Wittig reaction of the compound of the formula (If) with 2-dimethylaminoacetaldehyde;

wherein Ar, M and L are as defined in claim 1.

* * * * *